United States Patent
Ryan

(10) Patent No.: US 11,523,694 B2
(45) Date of Patent: Dec. 13, 2022

(54) ADJUSTABLE PILLOW

(71) Applicant: Matthew Adam Ryan, Gig Harbor, WA (US)

(72) Inventor: Matthew Adam Ryan, Gig Harbor, WA (US)

( * ) Notice: Subject to any disclaimer, the term of this patent is extended or adjusted under 35 U.S.C. 154(b) by 143 days.

(21) Appl. No.: 16/961,216

(22) PCT Filed: Jan. 8, 2019

(86) PCT No.: PCT/US2019/012616
§ 371 (c)(1),
(2) Date: Jul. 9, 2020

(87) PCT Pub. No.: WO2019/139873
PCT Pub. Date: Jul. 18, 2019

(65) Prior Publication Data
US 2020/0367672 A1    Nov. 26, 2020

Related U.S. Application Data

(60) Provisional application No. 62/616,304, filed on Jan. 11, 2018.

(51) Int. Cl.
*A47G 9/10* (2006.01)
*A47G 9/00* (2006.01)
*A61F 5/56* (2006.01)

(52) U.S. Cl.
CPC ........... *A47G 9/109* (2013.01); *A47G 9/1027* (2013.01); *A47G 2009/003* (2013.01);
(Continued)

(58) Field of Classification Search
CPC .... A47G 9/109; A47G 9/1081; A47G 9/1072; A47G 9/1063; A47G 9/1054;
(Continued)

(56) References Cited

U.S. PATENT DOCUMENTS 1,385,355 A    7/1921  Banks
2,199,479 A    5/1940  Cappel
(Continued)

FOREIGN PATENT DOCUMENTS

JP         4313254 B2    2/2005
KR    200471847 Y1    3/2014
(Continued)

*Primary Examiner* — Peter M. Cuomo
*Assistant Examiner* — George Sun
(74) *Attorney, Agent, or Firm* — Knobbe Martens Olson & Bear, LLP

(57) ABSTRACT

An adjustable orthopedic pillow includes a plurality of sections separated by dividers. Each section includes a head support fill chamber, a comfort layer fill chamber, a primary cervical support fill chamber, and a secondary cervical support fill chamber. The primary cervical support fill chamber can be positioned between at least a portion of the head support fill chamber and at least a portion of the comfort layer fill chamber and can an opening at a superior portion of the primary cervical support fill chamber. The secondary cervical support fill chamber can be positioned between at least a portion of the head support fill chamber and at least a portion of primary cervical support fill chamber and can include an opening at an inferior portion of the secondary cervical support fill chamber.

20 Claims, 14 Drawing Sheets

(52) U.S. Cl.
CPC ........ *A47G 2009/1018* (2013.01); *A61F 5/56* (2013.01); *A61H 2201/1609* (2013.01)

(58) Field of Classification Search
CPC ............ A47G 9/1027; A47G 2009/003; A47G 2009/1018; A61F 5/56; A61H 2201/1609
See application file for complete search history.

(56) References Cited

U.S. PATENT DOCUMENTS

| | | | |
|---|---|---|---|
| 2,500,974 A | 3/1950 | Angert | |
| 2,940,088 A | 6/1960 | Boos | |
| 3,400,413 A | 9/1968 | LaGrossa | |
| 3,667,074 A | 6/1972 | Emery | |
| 3,757,364 A * | 9/1973 | Downing | A47G 9/10 5/636 |
| 4,756,035 A * | 7/1988 | Beier | A47G 9/1081 5/643 |
| 4,908,894 A | 3/1990 | Sanders | |
| 5,014,377 A | 5/1991 | Dixon | |
| 5,016,303 A * | 5/1991 | Tanaka | A47G 9/109 5/636 |
| 5,018,231 A | 5/1991 | Wang | |
| 5,088,141 A | 2/1992 | Meyer | |
| 5,214,814 A | 6/1993 | Eremita | |
| 5,363,524 A | 11/1994 | Lang | |
| 5,367,731 A | 11/1994 | O'Sullivan | |
| 5,457,832 A | 10/1995 | Tatum | |
| 5,630,651 A | 5/1997 | Fishbane | |
| 5,661,862 A | 9/1997 | Ryndak | |
| 5,708,998 A | 1/1998 | Torbik | |
| 5,809,597 A * | 9/1998 | Shaw | A61G 7/0755 5/640 |
| 5,898,963 A * | 5/1999 | Larson | A47C 27/084 5/640 |
| 5,987,676 A | 11/1999 | Littleford | |
| 6,009,577 A | 1/2000 | Day | |
| 6,131,219 A * | 10/2000 | Roberts | A47G 9/1027 5/636 |
| 6,151,735 A * | 11/2000 | Koby | A47C 27/084 5/644 |
| 6,230,347 B1 * | 5/2001 | Alexander | A61F 5/01 5/636 |
| 6,317,908 B1 * | 11/2001 | Walpin | A47G 9/10 5/636 |
| 6,513,179 B1 | 2/2003 | Pan | |
| 6,671,906 B1 | 6/2004 | Milligan | |
| 6,931,682 B2 | 8/2005 | Kruger, Jr. | |
| 7,082,633 B1 | 8/2006 | Maarbjerg | |
| 7,152,263 B1 | 12/2006 | Delfs | |
| 7,203,983 B1 | 4/2007 | Reeves | |
| 7,513,002 B2 | 4/2009 | Best | |
| 7,562,405 B2 | 7/2009 | Brogan | |
| 7,578,015 B2 | 8/2009 | Wilson | |
| 7,681,263 B1 | 3/2010 | Hawkins | |
| 7,788,750 B2 | 9/2010 | Norstrem | |
| 8,707,485 B1 | 4/2014 | Conley | |
| 8,893,334 B1 | 11/2014 | Wong | |
| 9,113,732 B2 | 8/2015 | Loth | |
| 2003/0084511 A1 * | 5/2003 | Salvatini | A61G 1/00 5/423 |
| 2005/0217029 A1 * | 10/2005 | Funatogawa | A47G 9/109 5/636 |
| 2008/0086818 A1 * | 4/2008 | Sramek | A47G 9/10 5/636 |
| 2011/0056503 A1 * | 3/2011 | Abraham | A61F 5/56 128/845 |
| 2011/0252567 A1 * | 10/2011 | Yu | A47G 9/10 5/640 |
| 2013/0167298 A1 | 7/2013 | Grunstein | |
| 2013/0263377 A1 * | 10/2013 | Wootten, Jr. | A47G 9/10 5/640 |
| 2016/0213176 A1 * | 7/2016 | Clemente, II | A47G 9/1081 |

FOREIGN PATENT DOCUMENTS

| | | |
|---|---|---|
| KR | 200474184 Y1 | 9/2014 |
| WO | WO 2011/026260 A1 | 3/2011 |

* cited by examiner

ADJUSTABLE PILLOW

CROSS REFERENCE TO RELATED APPLICATIONS

This application is a U.S. National Phase Application of PCT International Application Number PCT/US2019/012616, filed on Jan. 8, 2019, designating the United States of America and published in the English language, which is an International Application of and claims the benefit of priority to U.S. Provisional Application No. 62/616,304, filed on Jan. 11, 2018. The disclosures of the above-referenced applications are hereby expressly incorporated by reference in their entireties.

FIELD OF THE INVENTION

Aspects of this invention relate to orthopedics, and more particularly, relates to orthopedic pillows and uses thereof.

DESCRIPTION OF THE RELATED ART

Various conditions such as neck pain, neck stiffness, back pain, back stiffness, sleep apnea, insomnia, snoring, and acid reflux may be associated with or aggravated by a position of the head and/or neck during sleep. A pillow that is too thick or too stiff can cause strained anatomical and structural positioning of the bony, muscular, ligamentous, neurological, and vascular integrated systems of the human body, which can result in neck or back pain and obstruction to the airway. Conversely, a pillow that does not provide sufficient support to the head can cause the head to angle upward, which may strain the neck muscles, reduce airflow through the respiratory system, and cause headaches and neck pain. Other conditions which may aggravate or be an underlying condition that can cause neck pain and/or neck stiffness include arthritis, degenerative joint disease, subluxation, intervertebral disk protrusion(s), vertebral artery occlusion or impediment (aggravation of tortuosity), muscular spasms, adhesions, contractures, unilateral shortening/abnormal unilateral tone, neurological compromise conditions (for example, nerve root compromise), cervical spine loss of lordosis, cervical spine straightening, cervical spine reversal, cervical spine deviation, and vertebral segmental instability due to ligament abnormalities. Orthopedic pillows have been designed to facilitate proper alignment of various parts of the body during sleep. An orthopedic pillow may have a defined shape or be formed of a particular material intended to facilitate proper alignment. Such pillows may be designed to be generally applicable to an average individual or a large population of individuals. Some manufacturers offer pillows that have different parameters based on user characteristics such as height, weight, age, and gender, as well as preferred sleeping conditions such as sleep position, mattress type, and pillow firmness. These pillows do not account for changes in a user's physical characteristics, changes in a user's orthopedic condition(s), or changes in user preferences over time.

SUMMARY

Aspects of the present application include systems, devices, and methods for providing orthopedic support.

Aspects of the present invention also include systems, devices, and methods for providing adaptive orthopedic support having variable-controlled adjustability.

In certain embodiments, an adjustable orthopedic pillow is disclosed. The adjustable orthopedic pillow comprises a plurality of sections, each section at least partially separated from adjacent sections by a divider extending from a rear surface of the pillow towards a front surface of the pillow. Each section comprises a head support fill chamber extending anteriorly from the rear surface of the pillow at least partially towards the front surface of the pillow and extending superiorly from a bottom surface of the pillow at least partially towards a top surface of the pillow, a comfort layer fill chamber positioned between the head support fill chamber and the top surface of the pillow and between the head support fill chamber and the front surface of the pillow, a primary cervical support fill chamber positioned between at least a portion of the head support fill chamber and at least a portion of the comfort layer fill chamber, the primary cervical support fill chamber comprising an opening at a superior portion of the primary cervical support fill chamber, and a secondary cervical support fill chamber positioned between at least a portion of the head support fill chamber and at least a portion of primary cervical support fill chamber, the secondary cervical support fill chamber comprising an opening at an inferior portion of the secondary cervical support fill chamber. In certain embodiments, the divider can be a sewn seam or a panel of fabric.

In certain embodiments, an adjustable orthopedic pillow is disclosed. The adjustable orthopedic pillow includes a head support fill chamber extending anteriorly from a rear surface of the pillow at least partially towards a front surface of the pillow and extending superiorly from a bottom surface of the pillow at least partially towards a top surface of the pillow, a comfort layer fill chamber positioned between the head support fill chamber and the top surface of the pillow and between the head support fill chamber and the front surface of the pillow, and a plurality of cervical support fill chambers positioned between the head support fill chamber and an anterior section of the comfort layer fill chamber, wherein at least one of the plurality of cervical support fill chambers includes an opening at a superior portion of the cervical support fill chamber and at least one of the cervical support fill chambers includes an opening at an inferior portion of the cervical support fill chamber.

In certain embodiments, an adjustable orthopedic pillow is disclosed. The adjustable orthopedic pillow includes a head support fill chamber extending anteriorly from a rear surface of the pillow at least partially towards a front surface of the pillow and extending superiorly from a bottom surface of the pillow at least partially towards a top surface of the pillow, a comfort layer fill chamber positioned between the head support fill chamber and the top surface of the pillow and between the head support fill chamber and the front surface of the pillow, and a cervical support fill chamber positioned between the head support fill chamber and an anterior section of the comfort layer fill chamber. The cervical support fill chamber includes a first end including an opening, a second end, and a channel extending between the first end and the second end, the channel including a first channel portion extending parallel to a front surface of the pillow and a second channel portion extending posteriorly from the first portion.

Aspects of the invention also include methods of using any of the aforementioned orthopedic pillows to reduce neck stiffness, to improve sleep, to reduce headaches, and to improve spinal alignment. Such methods are practiced by selecting a subject or a plurality of subjects that are in need of a reduction in neck stiffness, improved sleep, or improved spinal alignment and providing said subjects any one or more of the orthopedic pillows described herein. In some approaches, said subjects are selected by health care professionals after clinical evaluation and in other approaches said subjects are selected or identified by the manufacturer of the orthopedic pillows described herein as a class, group, or population of subjects that would receive a health benefit from use of any one or more of the orthopedic pillows described herein. In certain embodiments, methods of using any of the aforementioned orthopedic pillows include analysis, assessment, and recommended parameters of adjustment for variables afforded by a particular embodiment of the orthopedic pillow.

BRIEF DESCRIPTION OF THE DRAWINGS

The features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will now be described with additional specificity and detail through use of the accompanying drawings.

DETAILED DESCRIPTION

Figure 1:
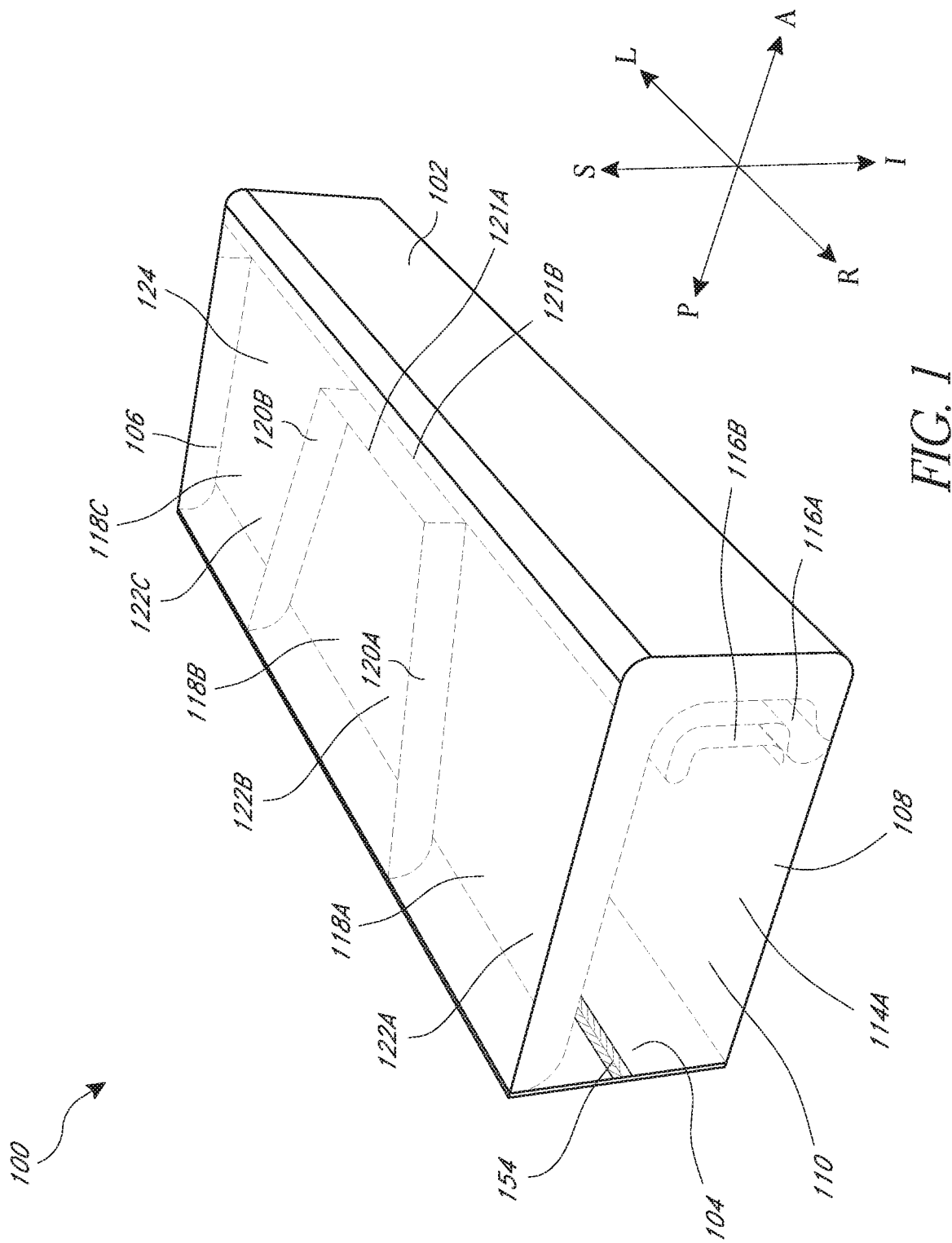
FIG. 1 depicts a perspective view of a pillow 100 according to an illustrative embodiment of the present invention showing interior features thereof.
Figure 2:
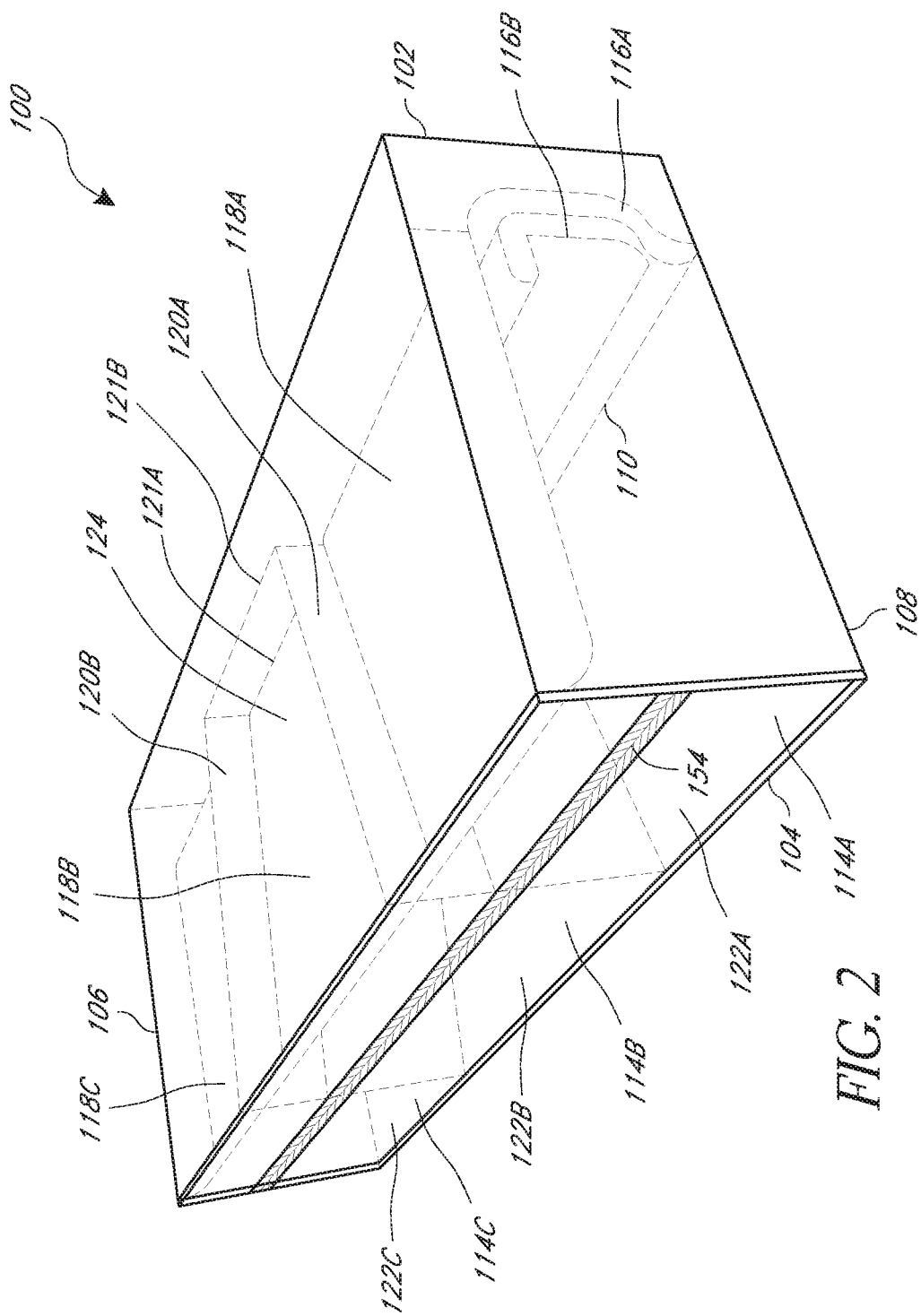
FIG. 2 depicts a perspective view of the pillow 100 showing interior features thereof.
Figure 3:
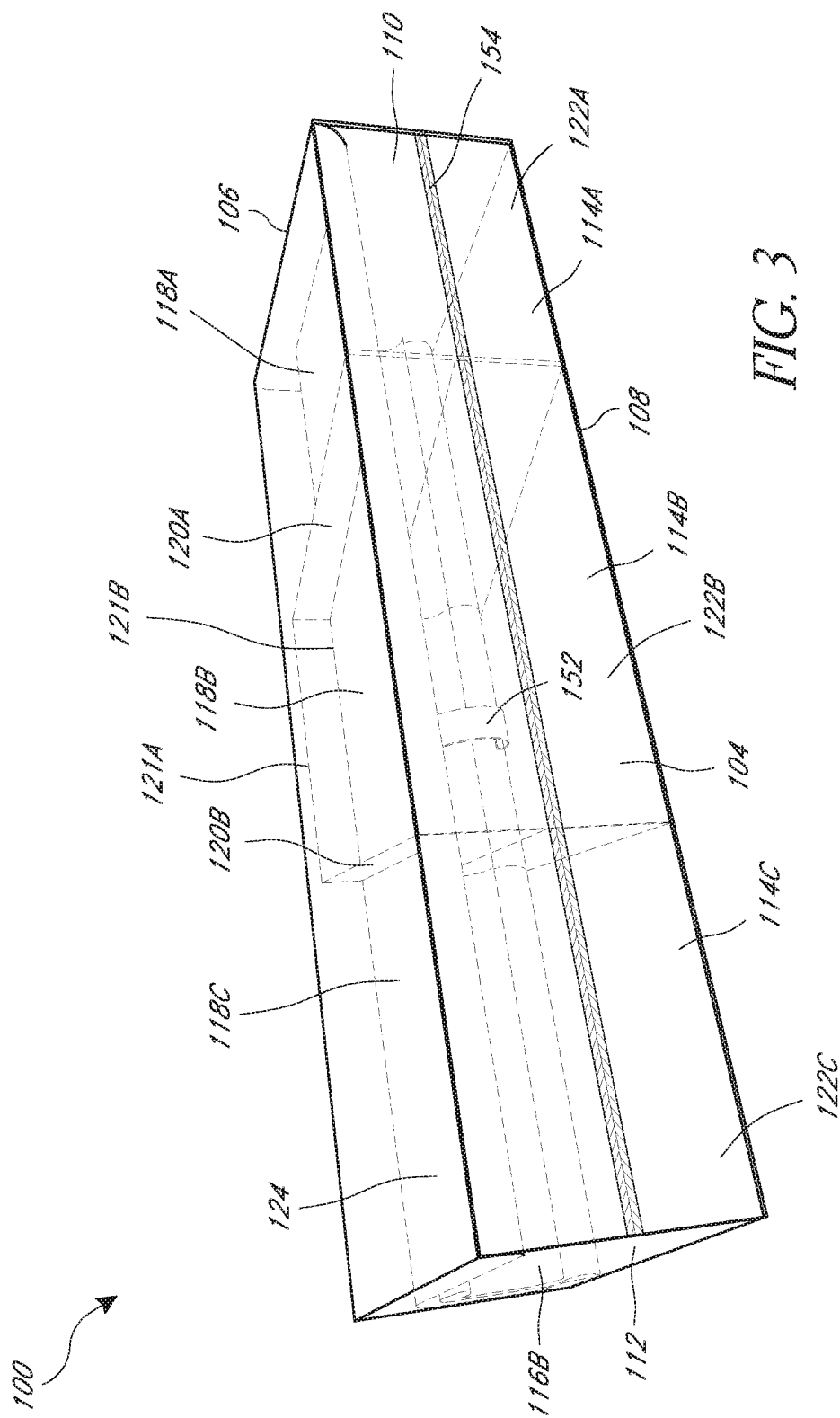
FIG. 3 depicts a perspective view of the pillow 100 showing interior features thereof.
Figure 4:
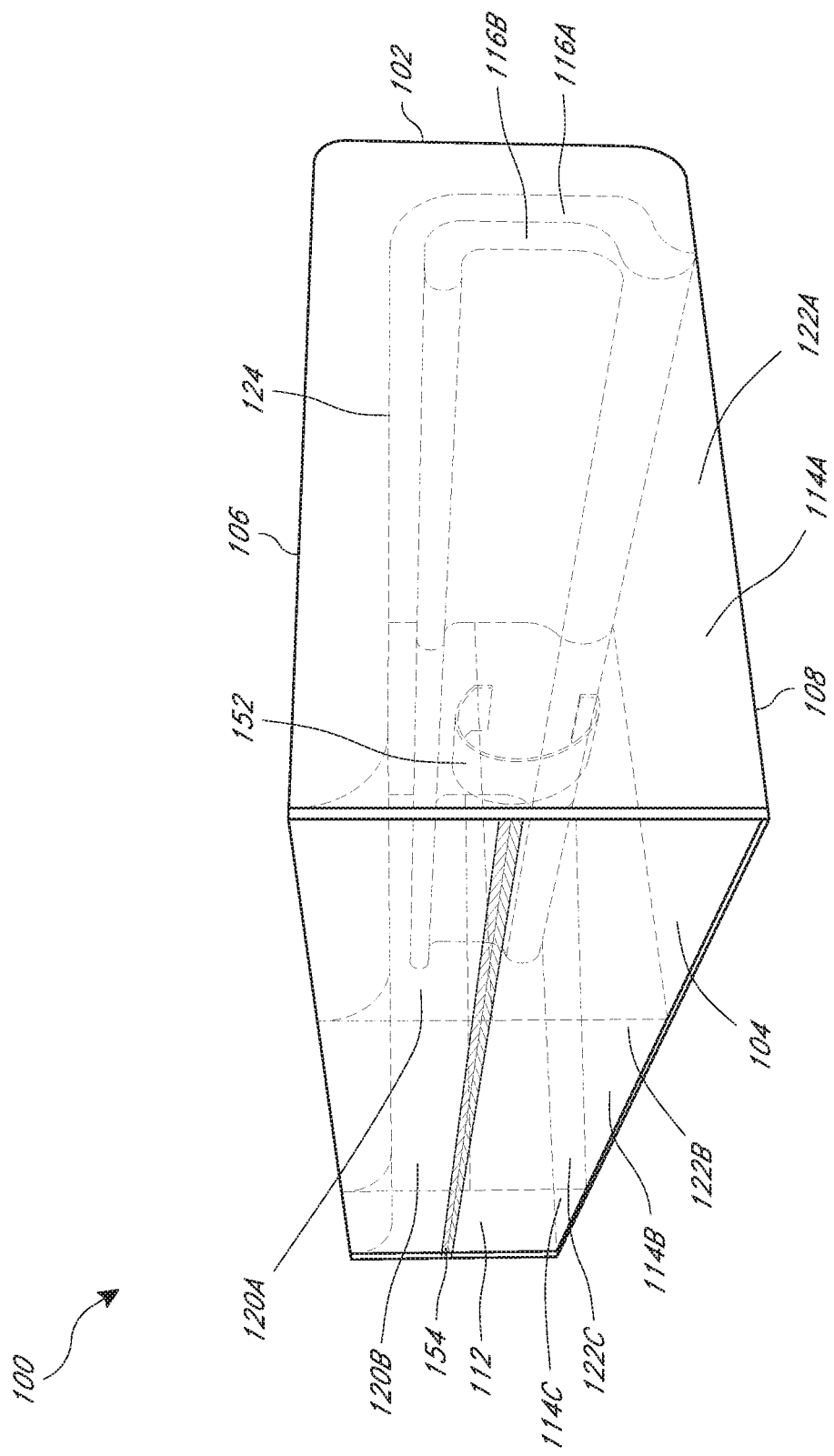
FIG. 4 depicts a perspective view of the pillow 100 showing interior features thereof.

The following detailed description is directed to certain specific embodiments. The invention(s) disclosed herein, however, can be embodied in a multitude of different ways as defined and covered by the claims. In this description, reference is made to the drawings, wherein like parts are designated with like numerals throughout. The features, aspects and advantages of the present invention will now be described with reference to the drawings of several embodiments that are intended to be within the scope of the development herein disclosed. These and other embodiments will become readily apparent to those skilled in the art from the following detailed description of the embodiments having reference to the attached figures, the invention not being limited to any particular embodiment(s) herein disclosed.

Methods, systems, and apparatuses are provided in certain embodiments of the present invention to provide orthopedic support to the head and neck of a user. In some embodiments, an adjustable orthopedic pillow is provided. The adjustable orthopedic pillow can include a plurality of chambers or compartments that can be separately filled with one or more materials to adjust a height, firmness, shape, or other quality of a section of the pillow.

In some embodiments, the adjustable orthopedic pillow can include one or more zippers, flaps, openings, doors, or other access features that can selectively allow access to the chambers from outside of the pillow. In some embodiments, the adjustable orthopedic pillow can include one or more dividers, doors, or flaps positioned to at least partially separate or partition individual chambers of the pillow. In some embodiments, the chambers of the pillow can be filled with one or more filling materials. In some embodiments, the filling materials can include one or more foam pieces. The foam pieces can be shaped, sized, or otherwise dimensioned to the provide support to a head or neck region of a user. In some embodiments, the foam pieces can be shaped, sized, or otherwise dimensioned to conform to the natural curvature of the cervical spine. In some embodiments, the filling materials can include one or more cervical rolls. A cervical roll can be cylindrical or any other suitable shape. In some embodiments, the cervical roll can be composed of or composed primarily of foam. The cervical roll can be positioned within the pillow to provide support to at least a portion of the cervical spine of a user.

In some embodiments, the adjustable orthopedic pillow can include one or more inflatable components. The one or more inflatable components can include one or more inflatable chambers that can be positioned in one or more sections or chambers of the pillow. The inflatable chambers can be inflated using a contained inflation fluid, such as air, water, gel or other thermo-regulatory fluid mediums, to adjust a height, firmness, shape, or other quality of a section of the pillow. The inflatable chambers can be shaped, sized, or otherwise dimensioned to the provide support to a head or neck region of a user when inflated. In some embodiments, the inflatable chambers can be shaped, sized, or otherwise dimensioned to conform to the natural curvature of the cervical spine when inflated. In some embodiments, at least one inflatable chamber can be positioned to provide support to at least a portion of the cervical spine of the user when inflated. In some embodiments, the inflatable chambers can be shaped, sized, or otherwise dimensioned to cause conformation of the cervical spine to a desired shape when inflated. In some embodiments, the inflatable chambers can be shaped, sized, or otherwise dimensioned to cause conformation of the cervical spine to a desired shape over time, for example, by sequentially causing conformation of the cervical spine to one or more different intermediate positions between an initial position and a desired final position through inflation of the inflatable chambers. In certain embodiments, the different positions of the spine between the initial position and the desired final position can be associated with different levels of inflation of one or more of the inflatable chambers.

In some embodiments, the adjustable orthopedic pillow can include one or more head support fill chambers. The head support fill chambers can be positioned with the pillow so that, when filled or at least partially filled with a material, the head support fill chambers support a portion of the head of a user when the user lies upon the pillow. In some embodiments, the adjustable orthopedic pillow can include one or more cervical support fill chambers. The cervical support fill chambers can be positioned within the pillow so that, when filled or at least partially filled with a material, the cervical support fill chambers support a portion of the cervical spine of a user when the user lies upon the pillow. In certain embodiments, each cervical support fill chamber can be filled incrementally. In certain embodiments, each cervical support fill chamber can be filled sequentially. In some embodiments, the adjustable orthopedic pillow can include one or more comfort layer fill chambers. The comfort layer fill chambers can be positioned between the head support fill chambers and/or cervical support fill chambers and a top surface of the pillow, between the head support fill chambers and/or cervical support fill chambers and a front surface of the pillow, and/or between the head support fill chambers and/or cervical support fill chambers and a bottom surface of the pillow. The comfort layer fill chambers can be positioned so that, when filled or at least partially filled with a material, the comfort layer fill chambers support a portion of the head and/or neck of the user when the user lies upon the pillow.

In some embodiments, the adjustable orthopedic pillow can include different chambers for accommodating different potential sleeping positions of a user. For example, the adjustable orthopedic pillow can include one or more chambers designed to support the head and/or neck of a user when the user is lying on their back and one or more chambers designed to support the head and/or neck of the user when the user is lying on their side. In some embodiments, the adjustable orthopedic pillow can include one or more chambers designed to support the head and/or neck of the user when the user is lying on their right side and one or more chambers designed to support the head and/or neck of the user when the user is lying on their left side.

FIGS. 1-5 depict an adjustable orthopedic pillow 100 according to an illustrative embodiment. In FIGS. 1-4, dashed lines are used to show internal features of the pillow 100. FIG. 1 also includes three-dimensional coordinate axes indicating the superior or upward ("S"), inferior or downward ("I"), anterior or frontward ("A"), posterior or rearward ("P") left ("L"), and right ("R") directions.

The pillow 100 includes a front or anterior surface 102, a rear or posterior surface 104, a top or superior surface 106, a bottom or inferior surface 108, a right side surface 110, and a left side surface 112, which form an exterior of the pillow. In use, the pillow 100 can be positioned so that the body of the user is generally anterior to the front surface 102 of the pillow 100 when the head and neck of the user are positioned on the pillow 100.

In certain embodiments, a distance between the rear surface 104 and the front surface 102 can be between 6 inches to 14 inches, between 8 inches to 12 inches, or 10 inches in length or within a range defined by any two of the aforementioned distances (e.g., 8 inches to 14 inches or 10 inches to 14 inches). In certain embodiments, a distance between the bottom surface 108 and the top surface 106 can be between 3 inches to 7 inches, between 4 inches to 6 inches, or 5 inches in length or within a range defined by any two of the aforementioned distances (e.g., 4 inches to 7 inches or 3 inches to 6 inches). In certain embodiments, a distance between the right side surface 110 and the left side surface 112 can be between 20 inches to 30 inches, between 22 inches to 28 inches, between 24 inches to 26 inches, or 25 inches in length or within a range defined by any two of the aforementioned distances (e.g., 22 inches to 30 inches or 24 inches to 28 inches).

In certain embodiments, the pillow includes a plurality of head support fill chambers 114A-114C. The head support fill chamber 114B can be positioned laterally between the head support fill chambers 114A and 114C. The head support fill chamber 114A can be positioned to the right of the head support fill chamber 114B, and the head support fill chamber 114C can be positioned to the left of the head support fill chamber 114B.

The head support fill chambers 114A-C can be selectively filled with one or more filling materials. Filling materials may include foam, fiber and/or a contained fluid, such as air, water, gel or other thermo-regulatory fluid mediums. In certain embodiments, when a filling material is positioned within the head support fill chambers 114A-C, the head support fill chambers 114A-C can provide positional support to the head of a user. In certain embodiments, the head support fill chamber 114A is designed to provide support to a user when the user is lying on their right side. In certain embodiments, the head support fill chamber 114B is designed to provide support to the head of a user when the user is lying on their back. In certain embodiments, the head support fill chamber 114C is designed to provide support to a user when the user is lying on their left side. Although three head support fill chambers 114A-C are described with respect to the pillow 100, the pillow 100 can include any number of head support fill chambers including 1, 2, 3, 4, 5, 6, or more head support fill chambers.

In certain embodiments, the adjustable orthopedic pillow 100 can include a plurality of cervical support fill chambers 116A-B. The cervical support fill chambers 116A-B can be positioned anterior to the head support fill chambers 114A-C, between the head support fill chambers 114A-C and the front surface 102 of the pillow 100. In certain embodiments, at least a portion of the cervical support fill chamber 116B is positioned between the head support fill chambers 1114A-C and the cervical support fill chamber 116A. In certain embodiments, the cervical support fill chambers 116A-B can extend between the right side surface 110 and the left side surface 112 of the pillow. In certain embodiments, the cervical support fill chamber 116A is a primary cervical support fill chamber and the cervical support fill chamber 116B is a secondary cervical support fill chamber.

The cervical support fill chambers 116A-B can be selectively filled with one or more filling materials. Filling materials may include foam, fiber and/or a contained fluid, such as air, water, gel or other thermo-regulatory fluid mediums. In certain embodiments, when a filling material is positioned within the cervical support fill chambers 116A-B, the cervical support fill chambers 116A-B can provide support to the cervical spine of a user. In certain embodiments, the primary cervical support chamber 116A is positioned to provide support to lower motion segments of the cervical spine of the user than the secondary cervical support chamber 116B. As used herein, a lower motion segment of the cervical spine refers to a motion segment that would be inferior when a user is standing in an upright position. In other words, a motion segment of the cervical spine is lower than another motion segment if it is further from the occipital-cervical junction or closer to the thoracic spine. Although two cervical support fill chambers 116A-B are described with respect to the pillow 100, the pillow 100 can include any number of cervical support fill chambers including 1, 2, 3, 4, 5, 6, 7, or more cervical support fill chambers.

In certain embodiments, the adjustable orthopedic pillow 100 can include a plurality of comfort layer fill chambers 118A-C. The comfort layer fill chambers 118A-C can be positioned between the head support fill chambers 114A-C and the exterior surfaces of the pillow 100 and between the cervical support fill chambers 116A-B and the exterior surfaces of the pillow 100. For example, at least a portion of the comfort layer fill chambers 118A-C can be positioned between the head support fill chambers 114A-C and the top surface 106 of the adjustable orthopedic pillow 100. In some embodiments, at least a portion of the comfort layer fill chambers 118A-C can be positioned between the cervical support fill chambers 116A-B and the front surface 102 of the adjustable orthopedic pillow 100. In certain embodiments, the comfort layer fill chambers can be positioned immediately inferior to the top surface 106 and immediately posterior to the front surface 102. In certain embodiments, the comfort layer fill chamber 118B can be positioned laterally between the comfort layer fill chambers 118A and 118C. The comfort layer fill chamber 118A can be positioned to the right of the comfort layer fill chamber 118B, and the comfort layer fill chamber 118C can be positioned to the left of the comfort layer fill chamber 118B.

In certain embodiments, one or more of the comfort layer fill chambers 118A-C may extend below the head support fill chambers 114A-C. For example in some embodiments, at least a portion of one or more of the comfort layer fill chambers 118A-C may be positioned between the head support fill chambers 114A-C and the bottom surface 108 of the pillow 100. In certain embodiments, one or more comfort layer fill chambers separate from the comfort layer fill chambers 118A-C may be positioned between the head support fill chambers 114A-C and the bottom surface 108 of the pillow 100.

The comfort layer fill chambers 118A-C can be selectively filled with one or more filling materials. Filling materials may include foam, fiber and/or a contained fluid, such as air, water, gel or other thermo-regulatory fluid mediums. The comfort layer fill chambers can be designed to provide a comfort interface between a user and the other chambers the pillow while the head and neck of the user are positioned on the adjustable orthopedic pillow 100. In certain embodiments, the comfort layer fill chamber can be filled with one or more materials that are softer, more pliable, more body-conforming, more or less heat absorbing, more or less heat transmitting, more or less heat dissipating, or otherwise more comfortable than the filling material within the head support fill chambers 114A-C and cervical support fill chambers 116A-B. In certain embodiments, when a filling material is positioned within the comfort layer fill chambers 118A-C, the comfort layer fill chambers 118A-C can provide support to the head of and/or cervical spine of a user. In certain embodiments, the chamber 118A is designed to provide support to a user when the user is lying on their right side. In certain embodiments, the chamber 118B is designed to provide support to a user when the user is lying on their back. In certain embodiments, the chamber 118C is designed to provide support to a user when the user is lying on their left side. Although three comfort layer fill chambers 118A-C are described with respect to the pillow 100, the pillow 100 can include any number of comfort layer fill chambers including e.g., 1, 2, 3, 4, 5, 6, or more comfort layer fill chambers.

In some embodiments, a plurality of dividers 120A-B can separate or at least partially separate the interior of the pillow 100 into a plurality of sections. In some embodiments, the dividers 120A-B can separate or at least partially separate the pillow into a first section 122A, a second section 122B, and a third section 122C. The first section 122A, second section 122B, and third section 122C can be a right section 122A, a center section 122B, and a left section 122C, respectively. The first section 122A can include the head support fill chamber 114A, the comfort layer fill chamber 118A, a portion of the primary cervical support fill chamber 116A between the head support fill chamber 114A and the comfort layer fill chamber 118A, and a portion of the secondary cervical support fill chamber 116B between head support fill chamber 114A and the comfort layer fill chamber 118A. The second section 122B can include the head support fill chamber 114B, the comfort layer fill chamber 118B, a portion of the primary cervical support fill chamber 116A between the head support fill chamber 114B and the comfort layer fill chamber 118B, and a portion of the secondary cervical support fill chamber 116B between head support fill chamber 114B and the comfort layer fill chamber 118B. The third section 122C can include the head support fill chamber 114C, the comfort layer fill chamber 118C, a portion of the primary cervical support fill chamber 116A between the head support fill chamber 114C and the comfort layer fill chamber 118C, and a portion of the secondary cervical support fill chamber 116B between head support fill chamber 114C and the comfort layer fill chamber 118C.

In certain embodiments, the divider 120A can separate at least a portion of the first section 122A from the second section 122B. In certain embodiments, the divider 120A can extend anteriorly from the rear surface 104 of the pillow 100. In some embodiments, the divider 120A can divide the head support fill chamber 114A from the head support fill chamber 114B. In some embodiments, the divider 120A can separate a portion of the comfort layer fill chamber 118A that is superior to the head support fill chamber 114A from a portion of the comfort layer fill chamber 118B that is superior to the head support fill chamber 114B. In some embodiments, the divider 120A can include a plurality of divider sections 120A. For example, a first divider section 120A may separate the head support fill chamber 114A from the head support fill chamber 114B, and a second divider section 120A may separate a portion of the comfort layer fill chamber 118A from a portion of the comfort layer fill chamber 118B. In some embodiments, the divider 120A or a divider section 120A can be a panel of fabric. In some embodiments, the divider 120A or a divider section 120A can be a sewn seam. For example, in some embodiments, a sewn seam between the top surface 106 and a surface defining a boundary between the head support fill chambers 114A-C and the comfort layer fill chambers 118A-C, for example, a divider 124, can act as a divider 120A or divider section 120A. In some embodiments, one or more divider sections 120A can be connected by one or more sewn seams. In some embodiments, the divider 120A can separate a portion of the secondary cervical support fill chamber 116B positioned anterior to the head support fill chamber 114A from a portion of the secondary cervical support fill chamber 116B positioned anterior to the head support fill chamber 114B. In some embodiments, the divider 120A can separate a portion of the primary cervical support fill chamber 116A positioned anterior to the head support fill chamber 114A from a portion of the primary cervical support fill chamber 116A positioned anterior to the head support fill chamber 114B. In some embodiments, the divider 120A extends from the rear surface 104 to the secondary cervical support fill chamber 116B. The edges of the divider 120A can be secured to the pillow 100 by sewn seams. For example, the edges of the divider 120A can be secured to the top surface 106, the bottom surface 108, the rear surface 104, and/or the secondary cervical support fill chamber 116B by sewn seams.

In certain embodiments, the divider 120B can separate at least a portion of the third section 122C from the second section 122B. In certain embodiments, the divider 120B can extend anteriorly from the rear surface 104 of the pillow 100. In some embodiments, the divider 120B can divide the head support fill chamber 114C from the head support fill chamber 114B. In some embodiments, the divider 120B can separate a portion of the comfort layer fill chamber 118C that is superior to the head support fill chamber 114C from a portion of the comfort layer fill chamber 118B that is superior to the head support fill chamber 114B. In some embodiments, the divider 120B can include a plurality of divider sections 120B. For example, a first divider section 120B may separate the head support fill chamber 114C from the head support fill chamber 114B, and a second divider section 120B may separate a portion of the comfort layer fill chamber 118C from a portion of the comfort layer fill chamber 118B. In some embodiments, the divider 120B or a divider section 120B can be a panel of fabric. In some embodiments, the divider 120B or a divider section 120B can be a sewn seam. For example, in some embodiments, a sewn seam between the top surface 106 and a surface defining a boundary between the head support fill chambers 114A-C and the comfort layer fill chambers 118A-C, for example, the divider 124, can act as a divider 120B or divider section 120B. In some embodiments, one or more divider sections 120A can be connected by one or more sewn seams. In some embodiments, the divider 120B can separate a portion of the secondary cervical support fill chamber 116B positioned anterior to the head support fill chamber 114C from a portion of the secondary cervical support fill chamber 116B positioned anterior to the head support fill chamber 114B. In some embodiments, the divider 120B can separate a portion of the primary cervical support fill chamber 116A positioned anterior to the head support fill chamber 114C from a portion of the primary cervical support fill chamber 116A positioned anterior to the head support fill chamber 114B. In some embodiments, the divider 120B extends from the rear surface 104 to the secondary cervical support fill chamber 116B. The edges of the divider 120B can be secured to the pillow 100 by sewn seams. For example, the edges of the divider 120B can be secured to the top surface 106, the bottom surface 108, the rear surface 104, and/or the secondary cervical support fill chamber 116B by sewn seams.

In certain embodiments, the dividers 120A and 120B can each extend along an angle with respect to the rear surface 104 and the front surface 102. In some embodiments, the divider 120A can extend anteriorly and leftward from the rear surface 104. In certain embodiments, the divider 120B can extend anteriorly and rightward from the rear surface 104. In some embodiments, the dividers 120A-B can both angle medially from the rear surface 104 toward the front surface 102 of pillow 100. The dividers 120A-B can be angled medially from the rear surface 104 toward the front surface 102 such that the head support fill chamber 114B and/or comfort layer fill chamber 118B are generally trapezoidal in shape. The head support fill chamber 114B and/or comfort layer fill chamber 118B can be smaller in measure in an anterior dimension than in a posterior dimension. In certain embodiments, an anterior dimension of the comfort layer fill chamber 118B and/or head support fill chamber 114B can be between 5 inches to 9 inches, between 6 inches to 8 inches, or 7 inches in length. In certain embodiments, a posterior dimension of the comfort layer fill chamber 118B and/or head support fill chamber 114B can be between 9 inches to 13 inches, between 10 inches to 12 inches, or 11 inches in length. In certain embodiments, each of the head support fill chambers 114A and 114C and/or the comfort layer fill chambers 118A and 118C can be shaped as irregular complementary trapezoids to the head support fill chamber 114B and/or comfort layer fill chamber 118B. The head support fill chambers 114A and 114C can be smaller in measure in a posterior dimension than in an anterior dimension. In certain embodiments, an anterior dimension of the head support fill chambers 114A and 114C and/or an anterior dimension of the comfort layer fill chambers 118A and 118C can be between 9 inches to 13 inches, between 10 inches to 12 inches, or 11 inches in length. In certain embodiments, a posterior dimension of the head support fill chambers 114A and 114C and/or an anterior dimension of the comfort layer fill chambers 118A and 118C can be between 5 inches to 9 inches, between 6 inches to 8 inches, or 7 inches in length. In some embodiments, the head support fill chambers 114A and 114C can be larger in measure in a posterior dimension than in an anterior dimension. The comfort layer fill chambers 118A and 118C can be smaller in measure in a posterior dimension than in an anterior dimension. In some embodiments, the comfort layer fill chambers 118A and 118C can be larger in measure in a posterior dimension than in an anterior dimension. In certain embodiments, an inferior edge and/or superior edge of each divider 120A and 120B can be chamfered to allow the pillow to provide a first side for an individual of a first size and a second side for an individual of a second size, greater than the first size.

In certain embodiments, a divider may extend laterally between anterior portions of the divider 120A and the divider 120B. The divider may include one or more panels or sheets of fabric and/or one or more seams. The divider can include a superior edge 121A and an inferior edge 121B. The edge 121A may be a seam between the divider and the top surface 106 of the pillow 100. The edge 121B can be a seam between the divider and a bottom surface of the comfort layer fill chamber 118B. In certain embodiments, the divider between edges 121A and 121B, the divider 120A, and/or the divider 120B can be positioned to align one or more filing material components within the comfort layer fill chamber 118B. In certain embodiments, the divider between edges 121A and 121B, the divider 120A and/or the divider 120B can be positioned to separate one or more filling material components within the comfort layer fill chamber 118B from filling material components within other chambers of the pillow 100.

In certain embodiments, the adjustable orthopedic pillow can include a divider 124 that can separate the head support fill chambers 114A-C and the primary cervical support fill chamber 116A from the comfort layer fill chambers 118A-C. In certain embodiments, the divider 124 can define a superior boundary of the head support fill chambers 114A-C and an anterior boundary of the primary cervical support fill chamber 116A. In some embodiments, the divider 124 can include a portion 126A that extends generally anteriorly from the rear surface 104 of the pillow 100 and forms a superior boundary of the head support fill chambers 114A-C. The divider 124 can also include a portion 126C that forms an anterior boundary of the primary cervical support fill chamber 116A. The divider 124 can also include a curved portion 126B extending between the portion 126A and the portion 126C. In some embodiments, the portion 126C extends generally inferiorly from the curved portion 126B. A curved portion 126D curves posteriorly from the portion 126C.

In certain embodiments, the divider 124 can be a single divider extending laterally across the pillow 100 to separate the head support fill chambers 114A-C from the comfort layer fill chambers 118A-C. In certain embodiments, the divider 124 may be a plurality of dividers 124 formed from one or more fabric sheets and/or sewn seams.

In certain embodiments, the comfort layer fill chambers 118A-C can each include a superior portion 160A positioned generally between the portion 126A of the divider and the superior surface 106. Each comfort layer fill chamber 118A-C can also include an elongated anterior portion 160B extending generally along the superior-inferior axis between the portion 126C and the anterior surface 102 of the pillow 100. In certain embodiments, each comfort layer fill chambers 118A-C can include a portion 160C extending posteriorly from an inferior end of the anterior portion 160B. The portion 160C can be defined by the portion 126D of the divider 124.

In certain embodiments, the divider 124 can include one or more flaps, zippers, doors, or other access features that can be opened to allow access between the head support fill chambers 114A-C and the comfort layer fill chambers 118A-C. The access features can allow for the movement of filling material between the head support fill chambers 114A-C and the comfort layer fill chambers 118A-C.

In certain embodiments, the divider 124 can include a superior end 128 and an inferior end 130. In certain embodiments, the superior end 128 can generally be in contact with one or more of the rear surface 104 and the superior surface 106 of the adjustable orthopedic pillow 100 to separate the head support fill chambers 114A-C from the comfort layer fill chambers 118A-C. In certain embodiments, the superior end 128 is secured to one or more of the rear surface 104 and the superior surface 106 through a sewn seam. In certain embodiments, superior end 128 of the divider 124 is movable away from the rear surface 104 and/or top surface 106 of the adjustable orthopedic pillow 100 to allow access between the head support fill chambers 114A-C and the comfort layer fill chambers 118A-C. In certain embodiments, the inferior end 130 of the divider 124 is generally in contact with inferior surface 108 of the pillow 100. In certain embodiments, the inferior end 130 is secured to the inferior surface 108 of the pillow 100 through a sewn seam. In certain embodiments, the inferior end 130 is movable away from the inferior surface 108, for example, in a superior direction, to allow for access between the head support fill chambers 114A-C and the comfort layer fill chambers 118A-C or to allow for access between the primary cervical support fill chamber 116A and the comfort layer fill chambers 118A-C.

Figure 5:
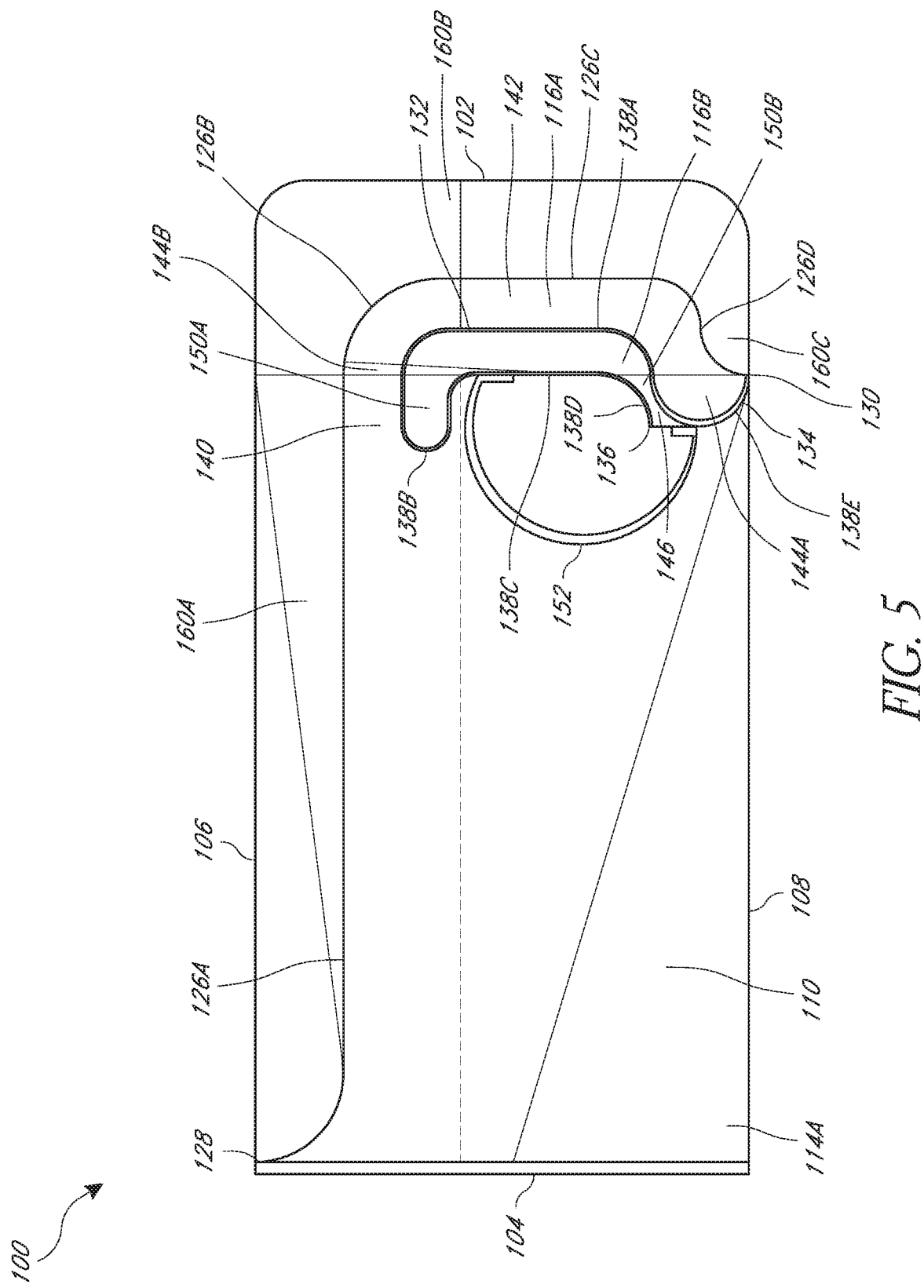
FIG. 5 depicts a cross-sectional view of the pillow 100.

In certain embodiments, the adjustable orthopedic pillow 100 can include a divider 132. The divider 132 can define the boundaries of the plurality of cervical support fill chambers 116A and 116B. In some embodiments, the divider 132 is a single continuous divider. In other embodiments, the divider 132 includes a plurality of separate divider sections. With reference to FIG. 5, the divider 132 can include a first end 134 and a second end 136. In certain embodiments, the first end 134 of the divider 132 can be generally in contact with the inferior end 130 of the divider 124. In certain embodiments, the first end 134 of the divider 132 can be generally in contact with the inferior surface 108 of the adjustable orthopedic pillow 100. In certain embodiments, the first end 134 can be movable to allow for access between the head support fill chambers 114A-C and the primary cervical support chamber 116A. In certain embodiments, the first end 134 can be movable to allow for access between the head support fill chambers 114A-C and the comfort layer fill chambers 118A-C.

In certain embodiments, the primary cervical support fill chamber 116A can be defined by the divider 124, which can define an anterior wall for the primary cervical support fill chamber 116A, and the divider 132, which can define a posterior wall of the primary cervical support fill chamber 116A. In certain embodiments, the section 126C of the divider 124 can form the anterior wall of the primary cervical support fill chamber 116A. In certain embodiments, the divider 132 can include a section 138A which defines a posterior wall of the primary cervical support fill chamber 116A. In certain embodiments, the primary cervical support fill chamber can include an opening 140 at a superior end of the primary cervical support fill chamber 116A. Alternatively, an opening can be provided at an inferior end of the primary cervical support fill chamber 116A. The opening 140 can allow for access between the primary cervical support fill chamber 116A and the head support fill chambers 114A-C. In certain embodiments, the primary cervical support fill chamber 116A can include an elongated section 142 that extends generally vertically, along the inferior-superior axis, within the pillow 100. In certain embodiments, the primary support fill chamber 116A can include a recessed portion 144A at an inferior end of the primary support fill chamber 116A. The recessed portion 144A can be recessed posteriorly from the elongated section 142 of the primary cervical support fill chamber 116A. The recessed portion 144A can be defined by the curved section 126D of the divider 124 and a curved section 138E of the divider 132. In certain embodiments, the primary cervical support fill chamber 116A can include a recessed portion 144B at a superior end of the primary cervical support fill chamber 116A. The recessed portion 144B can extend posteriorly from the elongated section 142 to the opening 140. The recessed section 144B can be defined by the section 126A and/or section 126B of the divider 124 and a curved section 138B of the divider 132.

In certain embodiments, the cervical support fill chamber 116B can be defined by the divider 132, which can form an anterior wall of the secondary cervical support fill chamber 116B, and a posterior wall of the secondary cervical support fill chamber 116B. In certain embodiments, the divider 132 can be a panel of fabric. In certain embodiments, the divider 132 can be secured to the right side 110 and the left side 112 of the pillow 100 by sewn seams at lateral edges of the divider 132. In certain embodiments, the section 138A of the divider 132 defines the anterior wall of the secondary cervical support fill chamber 116B. In certain embodiments, the divider 132 can include a section 138C which defines a posterior wall of the secondary cervical support fill chamber 116B. In certain embodiments, the divider 132 can include the curved section 138B that extends between the section 138A and the section 138C. In some embodiments, the curved section 138B extends posteriorly from the section 138A and then curves inferiorly and anteriorly to the section 138C. In certain embodiments, the secondary cervical support chamber 116B can include an opening 146 at an inferior end of the secondary cervical support fill chamber 116B. In alternative embodiments, the opening 146 can be positioned at a superior end of the secondary cervical support fill chamber 116B. The opening 146 can allow access between the secondary cervical support fill chamber 116B and the head support fill chambers 114A-C. In certain embodiments, the end 136 of the secondary cervical support fill chamber 116B can be movable to allow for an increase in the size of the opening 146. In certain embodiments, the secondary cervical support fill chamber 116B can include an elongated section 148 that extends generally vertically, along the inferior-superior axis, within the pillow 100. In certain embodiments, the secondary cervical support fill chamber 116B can include a recess portion 150A at a superior end of the secondary cervical support fill chamber 116B. The recessed portion 150A can be recessed posteriorly from the elongated section 150A of the secondary cervical support fill chamber 116B. In certain embodiments, the recessed section 150A can be defined by section 138B of the divider 132. In certain embodiments, the secondary cervical support fill chamber 116B can include a recessed portion 150B at an inferior end of the secondary cervical support fill chamber 116B. The recessed portion 150B can extend posteriorly from the elongated section 148 to the opening 146. The recessed section 150B can be defined by the curved portion 138E of the divider 132 that defines the recessed portion 134A of the primary cervical support fill chamber 116A and a curved section 138D between the section 138C and the end 136 of the divider 132. In certain embodiments, one or more of the sections 138A-E can be connected to one another at a lateral edge (right and/or left edge) by one or more sewn seams. For example, lateral edges of the section 138A may be secured to lateral edges of the section 138C. In some embodiments, the lateral edges of the section 138A may be secured to the lateral edges of the section 138C, and both the lateral edges of section 138A and the lateral edges of the section 138C can be secured to the side surfaces 110 and 112 of the pillow by one or more sewn seams. In certain embodiments, one or more of the sections 138A-E, one or more of the sections 126B-D, and/or the front surface 102 can be connected to one another at a lateral edge by one or more sewn seams. In certain embodiments, section 126A of the divider 124 can be connected to the top surface 106 at a lateral edge by one or more sewn seams.

As shown in FIG. 5, the secondary cervical support fill chamber 116B can be nested within the primary cervical support fill chamber 116A. As used herein, nested can mean that the entirety of the secondary cervical support chamber 116B or at least a portion of the secondary cervical support chamber 116B is positioned vertically, along the superior-inferior axis, between and/or in alignment with portions of the primary cervical support fill chamber 116A and/or positioned horizontally, along the anterior-posterior axis, between and/or in alignment with portions of the primary cervical support fill chamber 116B. In certain embodiments, the adjustable orthopedic pillow 100 can include e.g., 1, 2, 3, 4, 5, 6, 7, or more cervical support fill chambers. In certain embodiments, additional cervical support fill chambers can be added to an adjustable orthopedic pillow 100. The plurality of cervical support fill chambers can be in a nested configuration extending from the divider 132 posteriorly. Each posterior cervical support fill chamber can be nested within the cervical support fill chamber immediately anterior to it. Additional posterior cervical support chambers can provide an increased total length of cervical support and can support additional superiorly adjacent cervical vertebrae. In some embodiments, the plurality of cervical support fill chambers can include a series of alternating first cervical support fill chambers and second cervical support fill chambers extending posteriorly from the divider 132. Each first cervical support fill chamber can include an opening at a superior portion of the first cervical support fill chamber. Each second cervical support fill chamber can include an opening at an inferior portion of the secondary cervical support fill chamber. In some embodiments, the plurality of cervical support fill chambers can include a plurality of alternating second cervical support fill chambers and first cervical support fill chambers extending posteriorly from the divider 132.

In some embodiments, the adjustable orthopedic pillow 100 can include one or more straps 152 configured to receive one or more supports, such as a foam support, within the pillow 100. In some embodiments, the one or more straps 152 can include elastic bands or hook-and-loop fastener bands. In some embodiments, the one or more straps 152 can be sized, shaped, positioned, or otherwise configured to receive a cervical roll. In some embodiments, one or more straps 152 can extend posteriorly from the cervical support fill chambers 116A-B. In certain embodiments, the one more straps can be configured to secure one or more supports to the posterior wall of the cervical support fill chamber 116B. In some embodiments, each strap 152 can attach to the divider 132. In some embodiments, the one or more straps 152 can be configured to attach at a superior end to the section 138C of the divider 132 and at an inferior end to the section 138D of the divider. In some embodiments, the pillow 100 can include a single strap 152 positioned within the section 122B. In some embodiments, the pillow 100 can include a strap 152 in each of the sections 122A-C.

In certain embodiments, the adjustable orthopedic pillow 100 can include one or more zippers, flaps, doors, or other access features to allow access between the exterior of the pillow 100 and the chambers 114A-C, chambers 116A-B, and chambers 118A-C of the pillow 100. The access features can allow a user to introduce filling materials into the chambers 114A-C, chambers 116A-B. and/or chambers 118A-C of the pillow 100, remove filling materials from the chambers 114A-C, chambers 116A-B, and/or chambers 118A-C of the pillow 100, or move filling materials between the chambers 114A-C, chambers 116A-B. and/or chambers 118A-C of the pillow 100.

FIGS. 1-5 depict a zipper 154 along the posterior surface 104 of the pillow 100. The zipper can be opened to provide access to the head support fill chambers 114A-C. As described herein, various access features may allow for access to the cervical support fill chambers 116A-B and/or comfort layer fill chambers 118A-C from the head support fill chambers 114A-C. In certain embodiments, the pillow 100 can include a separate zipper or other access feature to allow access to each of the head support fill chamber 118A, the head support fill chamber 118B, and the head support fill chamber 118C. In certain embodiments, the pillow 100 can include one or more zippers or other access features that can be opened to allow direct access to one or more of the comfort layer fill chambers 118A-C. In certain embodiments, the pillow 100 can include one or more zippers or other access features that can be opened to allow direct access to one or more of the cervical support fill chambers 116A-B. In certain embodiments, the pillow 100 can include a fabric panel positioned posterior to or anterior to the zipper 154 to prevent or restrict the spillage of fill materials from the pillow 100 when the zipper 154 is opened or to prevent or restrict catching of materials in the zipper 154. In certain embodiments, the fabric panel can be integrally formed with the pillow 100. In other embodiments, the fabric panel may be detachable. In certain embodiments, the fabric panel can couple to the pillow 100 by one or more fasteners, for example, hook and loop (e.g., Velcro) or snap attachments. In certain embodiments, the panel can couple to the posterior surface 104 of the pillow. In certain embodiments, the panel can couple to a section of the posterior surface 104 defining pillow section 122B. In certain embodiments, the panel can couple to a posterior end of the dividers 120A and 120B. In certain embodiments, the panel can couple to a superior section of the dividers 120A and 120B. In certain embodiments, the panel can couple to one or more of the bottom surface 108, the top surface 106, and the posterior surface 104. In certain embodiments, a plurality of panels may be attached to the pillow 100. In certain embodiments, one or more panels can be positioned at exterior or interior sections of the pillow 100 adjacent to the zipper 154 and/or any other zippers to prevent or restrict spillage of materials from the pillow 100 and/or to prevent or restrict catching of materials in the zipper 154 or any other zippers of the pillow 100.

Figure 6:
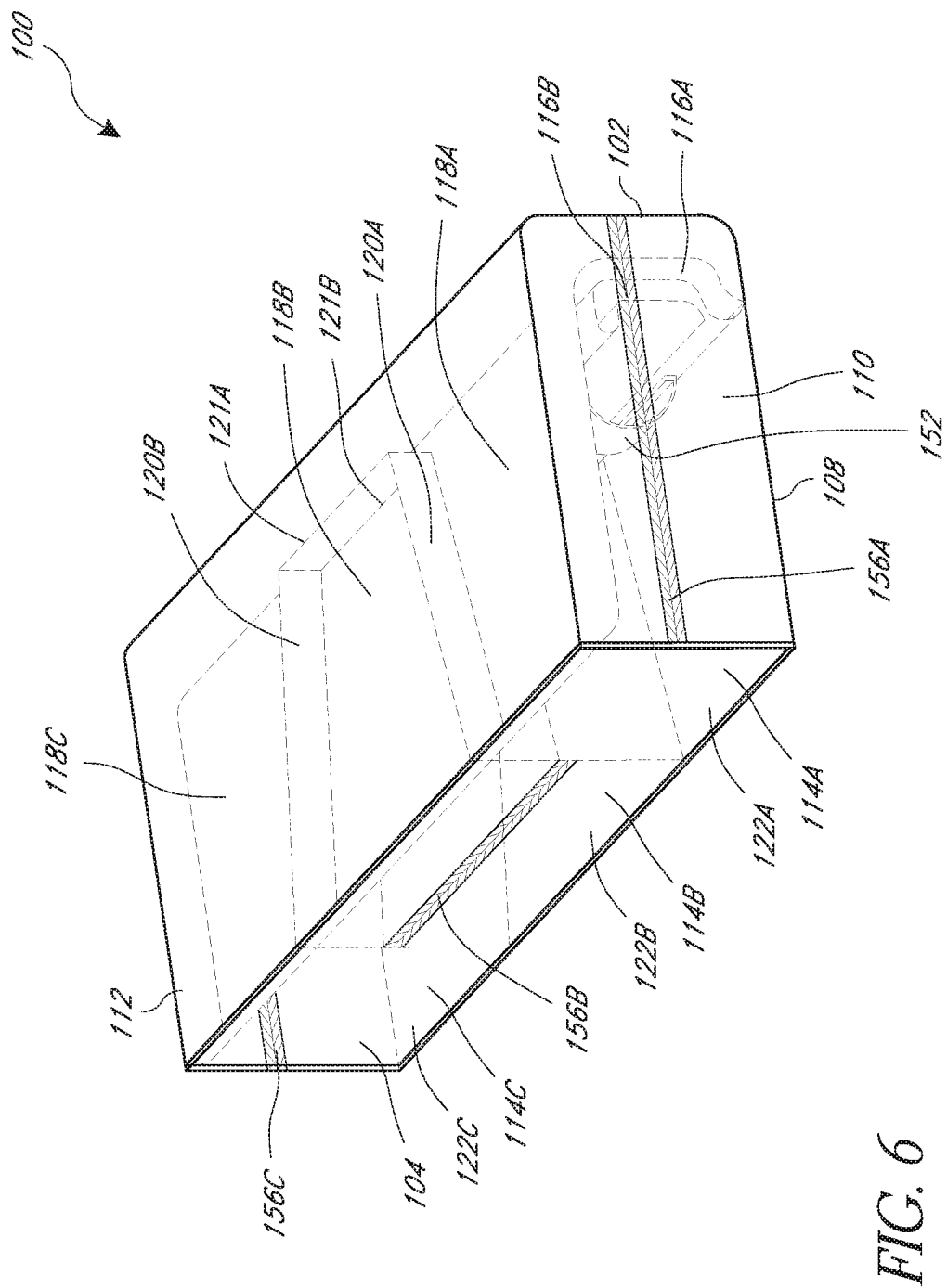
FIG. 6 depicts a perspective view of an alternative embodiment of the pillow 100 showing interior features thereof.

FIG. 6 depicts an embodiment of the pillow 100 showing an alternative zipper arrangement in which the pillow 100 includes a plurality of zippers 156A-C. Dashed lines are used to show internal features of the pillow 100. The zipper 156A is positioned on the right surface 110 and can be opened to provide access to the head support fill chamber 114A. The zipper 156B is positioned on the posterior surface 104 of the pillow and can be opened to provide access to the head support fill chamber. The zipper 156C is positioned on the left surface 112 and can be opened to provide access to the head support fill chamber 114C.

FIGS. 7-11 depict various embodiments of filling materials and filling material systems that can be used to fill the chambers 114A-C, 116A-B, and 118A-C of the pillow 100. The filling materials can include foam, fiber, memory foam, or any other suitable filling material. In some embodiments, the filling materials can include one or more inflatable filling materials configured to be filled with an inflation fluid. Such materials may include one or more polymers, for example, one or more polymer plastics. In some embodiments inflatable filling materials can include polyvinyl chloride, polyvinyl ethylene, and/or polyvinyl alcohol. In some embodiments, inflatable filling materials can include fabric reinforced polyvinyl chloride, fabric reinforced polyvinyl ethylene, and/or fabric reinforced polyvinyl alcohol. Filling materials can be introduced into, removed from, or moved between the chambers 114A-C, chambers 116A-B, and/or chambers 118A-C of the pillow 100 to provide desired levels of support and comfort and/or to provide various orthopedic treatments.

In some embodiments, the amount of filling materials within one of the head support fill chambers 114A and 114C can be increased or decreased to provide for support the normal curvature of the spine when a user is positioned on their side with their head positioned over the head support fill chamber 114A or the head support fill chamber 114C. In some embodiments, the amount of filling materials within one of the head support fill chambers 114A and 114C can be increased or decreased to provide a stressful support to correct abnormal positions and/or alignments of the spinal anatomy when a user is positioned on their side with their head positioned over the head support fill chamber 114A or the head support fill chamber 114C. For example, the amount of filling materials within one of the head support fill chambers 114A and 114C can be increased or decreased to reduce malalignment of the occiput, cervical spine, and/or thoracic spine, for example, to treat lateral misalignment, head tilt, and/or scoliosis of the cervical and/or thoracic spine. Such treatment can reduce stressors of the spine ligaments and discs, musculature, and/or neurological tissue. Such treatment may reduce vascular occlusions, restrictions, and/or impediments to vascular flow, and can allow proper drainage of the vasculature in the areas of the head and neck.

The amount of filling materials within the head support fill chambers 114A, 114B, and/or 114C can be increased or decreased when a user is positioned on their back with their head positioned over the head support fill chamber 114B to align the head in a centered position relative to the body. Aligning the head to a centered position relative to the body may cause spinal segmental and tissue alignment. Aligning the head to a centered position relative to the body may also improve or balance spatial position sensors of the semicircular canals of the inner ears and the spinal elements. Improvement or balancing of the spatial position sensors may decrease vertigo, neurological nausea, and/or anxiety. Improvement or balancing of the spatial position sensors may also decrease abnormal internal head blood pressure and pooling. Improvement or balancing of the spatial position sensors may also decrease neural tension of the dura mater, arachnoid mater, and neurological elements of the brain. Aligning the head to a centered position relative to the body may also reduce snoring, improve airflow, and reduce airway obstruction by the tongue. The amount of filling materials within the head support fill chamber 114B can be increased or decreased, when a user is positioned on their back with their head positioned over the head support fill chamber 114B, to reduce malalignment of the occiput, cervical spine, and/or thoracic spine, for example to reduce cervical kyphosis and/or to improve cervical lordosis. Such treatment can reduce stressors of the spine ligaments and discs, musculature, and/or neurological tissue. Such treatment can alleviate intervertebral disc pain, pressure, or strain. Such treatment may reduce vascular occlusions, restrictions, and/or impediments to vascular flow, and can allow proper drainage of the vasculature in the areas of the head and neck. Such treatment may also reduce snoring, improve airflow, and reduce airway obstruction by the tongue.

The amount of filling materials within primary cervical support fill chamber 116A can be increased or decreased to provide for support for the lower cervical spine when a user is positioned on their side with their neck positioned over the primary cervical support fill chamber 116A. Less pressure on the lower cervical spine may be desirable for users having more muscular trapezii than average, shorter necks than average, or swollen or irritated lower cervical structures and tissues. For such users, less filling material may be placed within the primary cervical support fill chamber 116A in comparison to an average individual. More pressure on the lower cervical spine may be desirable for users with less muscular trapezii or longer necks than average. More pressure on the lower cervical spine may also be desirable to treat a bulge in a lower cervical disc that is relieved with lateral pressure to the downward side of the spine contacting the pillow. For such users, more filling material may be placed within the primary support fill chamber 116A in comparison to an average individual.

The amount of filling materials within primary cervical support fill chamber 116A can be increased or decreased when a user is positioned on their back with their neck positioned over the primary cervical support fill chamber 116A to support the lower cervical spine and/or upper thoracic spine, to provide cervical lordosis support, to apply pressure to correct reversal of cervical lordosis, to correct cervical straightness, and/or to correct loss or reversal of spinal lordosis. For users having shorter cervical spines than average, the primary cervical support fill chamber provides cervical lordosis support and provide pressure to correct reversal of cervical lordosis. For users having average or longer than average cervical spines, the primary cervical support fill chamber can provide support for the lower cervical spine and/or upper thoracic spine, can apply pressure to correct cervical straightness, and provide pressure to correct loss or reversal of spinal lordosis, for example, when filled to a greater amount than necessary for supporting the natural state of alignment of the user.

The amount of filling materials within secondary cervical support fill chamber 116B can be increased or decreased when a user is positioned on their side with their neck positioned over the secondary cervical support fill chamber 116B to add firmness or buttress the primary cervical support fill chamber 116A to add lower cervical spine lateral pressure greater than the pressure or firmness of the head support fill chamber over which the user is positioned.

The amount of filling materials within secondary cervical support fill chamber 116B can be increased or decreased to provide when a user is positioned on their back with their neck positioned over the secondary cervical support fill chamber 116B to augment or buttress the support provided by the primary cervical support fill chamber 116A, or to add length to the lordosis support of the middle-lower cervical spine segments in combination with the primary cervical support fill chamber 116A. Adding length to the lordosis support for the middle-lower cervical spine segments may be desirable for users having cervical spines of average or above average length. In certain embodiments, additional cervical support fill chambers can be added posterior to the secondary cervical support fill chamber to provide support to the middle and middle-upper cervical spine segments. The additional cervical support fill chambers may individually provide more or less support to the motion segments of the spine or buttress support provided by more anterior cervical support fill chambers, such as the primary cervical support fill chamber 116A or secondary cervical support fill chamber 116B.

In certain embodiments, one or more foam supports, such as a cervical roll, can be secured to the cervical support fill chambers 116A-B to control an amount of pressure applied to the middle and lower cervical segments of the spine when the user is lying on their side or back. In certain embodiments, the application of pressure applied by the one or more foam supports can affect position support or shape of the spine and its related structures in the middle and lower cervical segments.

In certain embodiments, the amount of filling materials within one of the comfort layer fill chambers 118A and 118C can be increased or decreased when a user is positioned on their side with their head positioned over the comfort layer fill chamber 118A or the comfort layer chamber 118C to provide pressure sensitivity relief, improved feel, improved comfort, temperature control, or moisture control. In some embodiments, the amount of filling materials within one of the comfort layer fill chambers 118A and 118C can be increased or decreased when a user is positioned on their side with their head positioned over the comfort layer fill chamber 118A or the comfort layer chamber 118C to change the height or length of the pillow or to change a pressure or height ratio relative to a fill material composition of a head support fill chamber.

The amount of filling materials within the comfort layer fill chamber 118B can be increased or decreased when a user is positioned on their back with their head positioned over the head support fill chamber 114B to provide pressure sensitivity relief, improved feel, improved comfort, temperature control, or moisture control. In some embodiments, the amount of filling materials within the comfort layer fill chamber 118B can be increased or decreased when a user is positioned on their back with their head positioned over the head support fill chamber 118B to change the height or length of the pillow or to change a pressure or height ratio relative to a fill material composition of a head support fill chamber.

Together, the head support fill chambers 114A-C, cervical support fill chambers 116A-B. and/or comfort layer fill chambers 118A-C can be adjusted by introducing, removing, or rearranging filling material to conform with or support the normal lordotic curvature of the cervical spine. In certain embodiments, the one or more of the head support fill chambers 114A-C, cervical support fill chambers 116A-B, and comfort layer fill chambers 118A-C can be adjusted by introducing, removing, or rearranging filling material to realign the curvature of the cervical spine to its proper alignment. Although the examples discussed above describe a user positioned on their back with their head positioned over head support fill chamber 114B, positioned on their right side with their head positioned over head support fill chamber 114A, or positioned on their left side with their head positioned over head support fill chamber 114C, it should be understood that a user may choose to be positioned on their left side, right side, or back, while their head is positioned over any one of the head support fill chambers 114A-C.

In certain embodiments, one or more components of the pillow 100 can be made or formed of an elastic and/or deformable material configured to allow for stretching or expanding of the material when a head or neck of a user is positioned on the pillow 100. For example, in certain embodiments, the top surface 106 is formed or made of an elastic and/or deformable material. In certain embodiments, only a portion of the top surface 106 is made or formed of an elastic and/or deformable material. For example, only a portion of the top surface 106 defining one of the comfort layer fill chambers 118A, 118B, or 118C can be made or formed of an elastic and/or deformable material. Alternatively, a portion of the top surface 106 defining one of the comfort layer fill chambers 118A, 118B, or 118C or a section of the portion of the top surface 106 defining one of the comfort layer fill chambers 118A, 118B, or 118C can be made or formed of a material that is more elastic and/or more deformable than the portions of the top surface 106 defining the other comfort layer fill chambers 118A, 118B, or 118C. For example, in certain embodiments, the portion of the top surface 106 defining comfort layer fill chamber 118B or a section of the portion of the top surface 106 defining comfort layer fill chamber 118B can be formed or made of a material that is more elastic and/or more deformable than the material forming the portion of the top surface 106 defining the comfort layer fill chambers 118A and 118C. In such embodiments, when a head or neck of the user is positioned over the comfort layer fill chamber 118B, the elastic and/or deformable material of the top surface 106 can stretch to restrict or inhibit movement of the pillow sections 122A and 122C towards the head or neck of the user or towards the pillow section 122B.

In certain embodiments, the divider 124 is formed or made of an elastic and/or deformable material. In certain embodiments, only a portion of the divider 124 is formed or made of an elastic material and/or deformable material. For example, only a portion of the divider 124 defining one of the comfort layer fill chambers 118A, 118B, or 118C can be formed or made of an elastic material and/or deformable material. Alternatively, a portion of the divider 124 defining one of the comfort layer fill chambers 118A, 118B, or 118C or a section of the portion of the divider 124 defining one of the comfort layer fill chambers 118A, 118B, or 118C can be formed or made of a material that is more elastic or more deformable than the portions of the divider 124 defining the other comfort layer fill chambers 118A, 118B, or 118C. For example, in certain embodiments, the portion of the divider 124 defining comfort layer fill chamber 118B or a section of the portion of the divider 124 defining comfort layer fill chamber 118B can be formed or made of a material that is more elastic or more deformable than the material forming the portion of the divider 124 defining the comfort layer fill chambers 118A and 118C. In such embodiments, when a head or neck of the user is positioned over the comfort layer fill chamber 118B, the elastic and/or deformable material of the divider 124 can stretch to restrict or inhibit movement of the pillow sections 122A and 122C towards the head or neck of the user or towards the pillow sections 122B.

In certain embodiments, the bottom surface 108 is formed or made of an elastic and/or deformable material. In certain embodiments, only a portion of the bottom surface 108 is formed or made of an elastic material and/or deformable. For example, only a portion of the bottom surface 108 defining one of the head support fill chambers 114A, 114B, or 114C can be formed or made of an elastic and/or deformable material. Alternatively, a portion of the bottom surface 108 defining one of the head support fill chambers 114A, 114B, or 114C or a section of the portion of the bottom surface 108 defining one of the head support fill chambers 114A, 114B, or 114C can be formed or made of a material that is more elastic or more deformable than the portions of the bottom surface 108 defining the other head support fill chambers 114A, 114B, or 114C. For example, in certain embodiments, the portion of the bottom surface 108 defining head support fill chamber 114B or a section of the portion of the bottom surface 108 defining head support fill chamber 114B can be formed or made of a material that is more elastic or more deformable than the material forming the portion of the bottom surface 108 defining the head support fill chambers 114A and 114C. In such embodiments, when a head or neck of the user is positioned over the head support fill chamber 114B, for example if the pillow 100 is rotated so that the head of the user directly contacts the bottom surface 108, the elastic and/or deformable material of the bottom surface 108 can stretch to restrict or inhibit movement of the pillow sections 122A and 122C towards the head or neck of the user or towards the pillow sections 122B.

Figure 7:
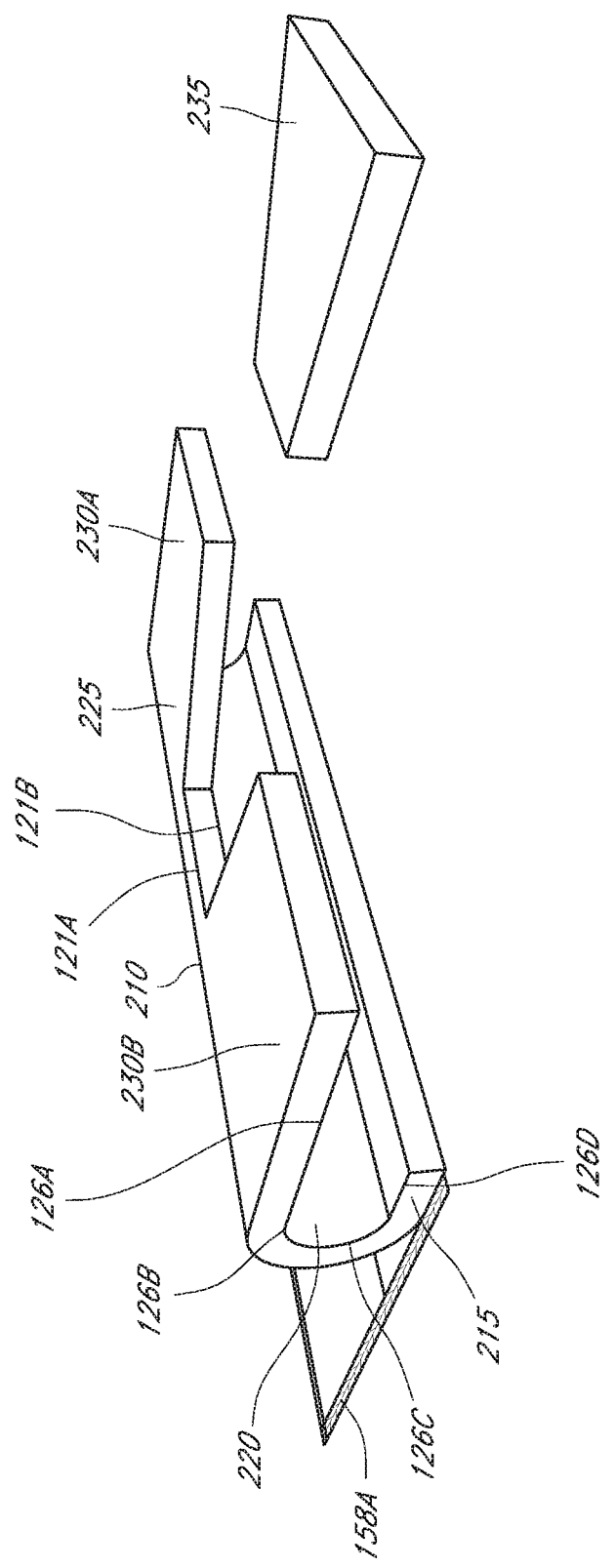
FIG. 7 depicts a perspective view of an attachable fill assembly that can be used with a pillow according to an illustrative embodiment of the present invention.

FIG. 7 depicts an embodiment of an encased attachable fill assembly that can attach to an adjustable orthopedic pillow, such as the pillow 100. The attachable fill assembly can include sheet(s) of fabric encasement having a zipper portion 158A at both a right and left lateral edge. The zipper portion 158A can be configured to secure to a complementary zipper portion on an adjustable orthopedic pillow 100. For example, in some embodiments, the zipper portion 158A can be configured to secure to a complementary zipper portion extending along a top surface and an anterior surface of an adjustable orthopedic pillow.

In certain embodiments, the attachable fill assembly can attach to an adjustable orthopedic pillow to form one or more comfort layer fill chambers, such as comfort layer fill chambers 118A-C. The attachable fill assembly includes a first filling material piece 210 and a second filling material piece 235. The first filling material piece 210 and second filling material piece 235 may be flexible, inflatable, or otherwise manipulable. The first filling material piece 210 and second filling material piece 235 are shown positioned in an example of a configuration when attached to an adjustable orthopedic pillow. The first piece 210 may have an inferior section 215, an anterior section 220, and a superior section 225. The anterior section 220 connects the inferior section 215 and the superior section 225. In some embodiments, the anterior section 220 is curved when attached to an adjustable orthopedic pillow. In certain embodiments, the superior section 225 includes a right section 230A and a left section 230B. The first filling material piece 210 can include portions 126A-D that form a divider, such as divider 124 as described with respect to FIGS. 1-6, between the comfort layer fill chambers of the attachable fill assembly and the head support fill chambers and cervical support fill chambers of an adjustable orthopedic pillow when the attachable fill assembly is attached to the adjustable orthopedic pillow, The first filling material piece 210 can also include edges 121A and 121B, which can define a divider that can align the second piece 235 within an adjustable orthopedic pillow.

In certain embodiments, filling material pieces 210 and 235 can be used in adjustable orthopedic pillows in which the comfort layer fill chambers are permanently attached to the adjustable orthopedic pillow, for example, the embodiments of the pillow 100 described with respect to FIGS. 1-6. In certain embodiments, the inferior section 215 can be positioned within an inferior portion 160C of the comfort layer fill chambers 118A-C. In certain embodiments, the inferior section 215 can extend into the head support fill chambers 114A-C. In certain embodiments, the inferior section 215 can extend into one or more comfort layer fill chambers positioned below the head support fill chambers 114A-C. In certain embodiments, the anterior section 220 can extend generally from the inferior portion 160C of each comfort layer fill chamber 118A-C through the anterior portion 160B and into the superior portion 160A. The right section 230A of the piece 210 can be positioned within the superior portion 160A of the comfort layer fill chamber 118A. The left section 230B of the piece 210 can be positioned within the superior portion 160A of the comfort layer fill chamber 118C. The piece 235 can be positioned within the superior portion 160A of the comfort layer fill chamber 118B. In certain embodiments, the piece 235 can be generally trapezoidal in shape. The sections 230B and 230A of the piece 210 can be defined by irregular trapezoid shapes.

Figure 8:
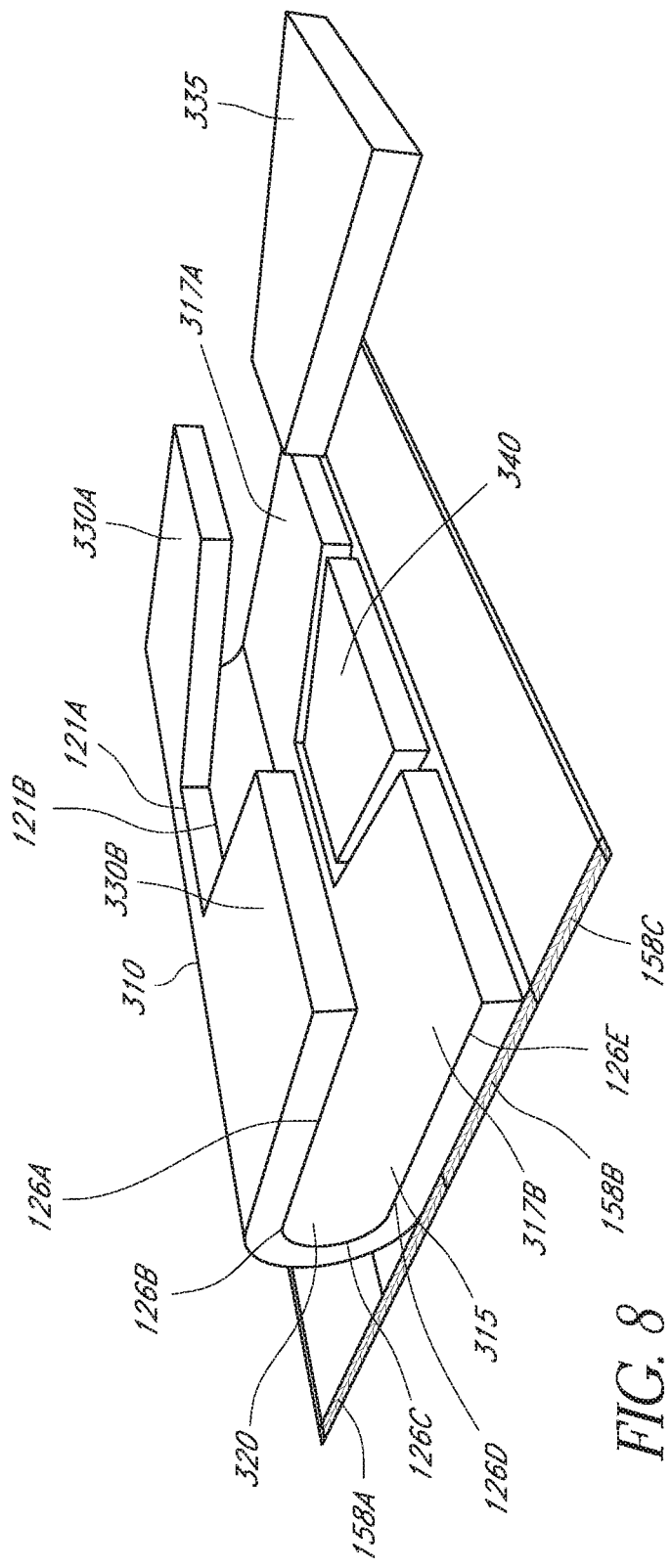
FIG. 8 depicts a perspective view of an attachable fill assembly that can be used with a pillow according to an illustrative embodiment of the present invention.

FIG. 8 depicts an embodiment of an encased attachable fill assembly that can attach to an adjustable orthopedic pillow, such as the pillow 100. The encased attachable fill assembly can include a sheet(s) of fabric having a zipper portion 158A at both a right and a left lateral edge. The zipper portion 158A can be configured to secure to a complementary zipper portion on an adjustable orthopedic pillow 100. For example, in some embodiments, the zipper portion 158A can be configured to secure to a complementary zipper portion extending along a top surface and an anterior surface of an adjustable orthopedic pillow. The sheet of fabric can also include a zipper portion 158B at each lateral edge. The zipper portion 158B can be configured to secure to a complementary zipper portion on an adjustable orthopedic pillow 100. For example, in some embodiments, the zipper portion 158B can be configured to secure to a complementary zipper portion extending along a bottom surface of an adjustable orthopedic pillow. The encasing sheet(s) of fabric can also include a zipper portion 158C at each lateral edge. The zipper portion 158C can be configured to secure to a complementary zipper portion on an adjustable orthopedic pillow 100. For example, in some embodiments, the zipper portion 158C can be configured to secure to a complementary zipper portion extending along a rear surface of an adjustable orthopedic pillow.

In certain embodiments, the attachable fill assembly can attach to an adjustable orthopedic pillow to form one or more comfort layer fill chambers, such as comfort layer fill chambers 118A-C. In certain embodiments, the attachable fill assembly can attach to an adjustable orthopedic pillow to form a comfort layer fill chamber along a bottom surface of an adjustable orthopedic pillow. The attachable fill assembly includes a first filing material piece 310, a second piece 335, and a third piece 340. The first filling material piece 310, second piece 335, and third piece 340 may be flexible, inflatable, or otherwise manipulable. The first filling material piece 310, second piece 335, and third piece 340 are shown positioned in an example of a configuration when attached to an adjustable orthopedic pillow. The first piece 310 has an inferior section 315, an anterior section 320, and a superior section 325. The anterior section 320 connects the inferior section 315 and the superior section 325. In some embodiments, the anterior section 320 can be curved. In certain embodiments, the superior section 325 includes a right section 330A and a left section 330B. The inferior section 315 can include a right section 317A and a left section 317B.

The first filling material piece 310 can include portions 126A-D that form a divider, such as divider 124 as described with respect to FIGS. 1-6, between the comfort layer fill chambers of the attachable fill assembly and the head support fill chambers and cervical support fill chambers of an adjustable orthopedic pillow when the attachable fill assembly is attached to the adjustable orthopedic pillow. In certain embodiments, the first filing material piece 310 can include a portion 126E. The portion 126E can form a divider between the comfort layer fill chambers of the attachable fill assembly and a bottom surface of the pillow inferior to the head support fill chambers when the attachable fill assembly is attached to the adjustable orthopedic pillow. The first filling material piece 310 can also include edges 121A and 121B, which can define a divider that can align the second piece 335 within an adjustable orthopedic pillow.

In certain embodiments, the first filling material piece 310, second piece 335, and third piece 340 can be used in adjustable orthopedic pillows in which the comfort layer fill chambers are permanently attached to the adjustable orthopedic pillow, for example, the embodiments of the pillow 100 described with respect to FIGS. 1-6. In certain embodiments, the inferior section 315 can be positioned within an inferior portion 160C of the comfort layer fill chambers 118A-C and can extend into the head support fill chambers 114A and 114C. In certain embodiments, the right section 317A can extend into the head support fill chamber 114A. In some embodiments, the right section 317A can extend into a comfort layer fill chamber positioned inferior to the head support fill chamber 114A. In certain embodiments, the left section 317B can extend into the head support fill chamber 114C. In some embodiments, the right section 317B can extend into a comfort layer fill chamber positioned inferior to the head support fill chamber 114C. In certain embodiments, the anterior section 320 can extend generally from the inferior portion 160C of each comfort layer fill chamber 118A-C through the anterior portion 160B and into the superior portion 160A. The right section 330A of the piece 310 can be positioned within the superior portion 160A of the comfort layer fill chamber 118A. The left section 330B of the piece 310 can be positioned within the superior portion 160A of the comfort layer fill chamber 118C. The piece 335 can be positioned within the superior portion 160A of the comfort layer fill chamber 118B. In certain embodiments, the piece 335 and/or the piece 340 can be generally trapezoidal in shape. The sections 317A and 317 can be defined by irregular trapezoid shapes. The sections 330A and 330B can be defined by irregular trapezoid shapes.

Figure 9:
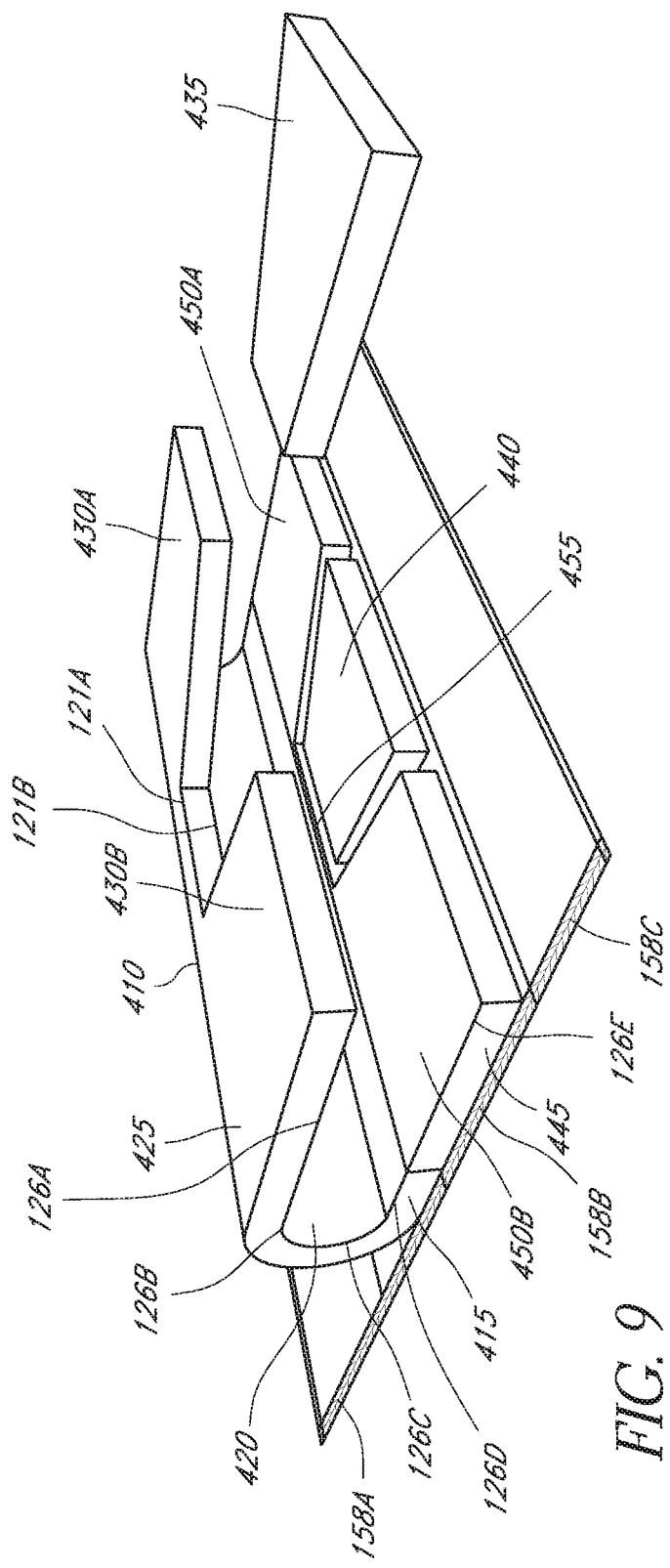
FIG. 9 depicts a perspective view of an attachable fill assembly that can be used with a pillow according to an illustrative embodiment of the present invention.

FIG. 9 depicts an embodiment of an attachable fill assembly that can attach to an adjustable orthopedic pillow, such as the pillow 100. The attachable fill assembly can include encasing sheet(s) of fabric having zipper portions 158A, 158B, and 158C as described with respect to FIG. 8.

In certain embodiments, the attachable fill assembly can attach to an adjustable orthopedic pillow to form one or more comfort layer fill chambers, such as comfort layer fill chambers 118A-C. In certain embodiments, the attachable fill assembly can attach to an adjustable orthopedic pillow to form a comfort layer fill chamber along a bottom surface of an adjustable orthopedic pillow. The attachable fill assembly includes a first filling material piece 410, a second filling material piece 435, a third filling material piece 440, and a fourth filling material piece 445. The first filing material piece 410, second filling material piece 435, third filling material piece 440, and fourth filling material piece 445 may be flexible, inflatable, or otherwise manipulable. The first filing material piece 410, second filling material piece 435, third filling material piece 440, and fourth filling material piece 445 are shown positioned in an example of a configuration when attached to an adjustable orthopedic pillow. The first piece 410 has an inferior section 415, an anterior section 420, and a superior section 425. The anterior section 420 connects the inferior section 415 and the superior section 425. In some embodiments, the anterior section 420 can be curved. In certain embodiments, the superior section 425 includes a right section 430A and a left section 430B. The fourth filling material piece 445 can include a right section 450A, a left section 450B, and a connection section 455 extending between the right section 450A and the left section 450B.

The first filling material piece 410 can include portions 126A-D that form a divider, such as divider 124 as described with respect to FIGS. 1-6, between the comfort layer fill chambers of the attachable fill assembly and the head support fill chambers and cervical support fill chambers of an adjustable orthopedic pillow when the attachable fill assembly is attached to the adjustable orthopedic pillow. In certain embodiments, the fourth filling material piece 445 can include a portion 126E. The portion 126E can form a divider between the comfort layer fill chambers of the attachable fill assembly and a bottom surface of the head support fill chambers when the attachable fill assembly is attached to the adjustable orthopedic pillow. The first filling material piece 410 can also include edges 121A and 121B, which can define a divider that can align the second piece 435 within an adjustable orthopedic pillow.

In certain embodiments, first filing material piece 410, second filling material piece 435, third filling material piece 440, and fourth filling material piece 445 can be used in adjustable orthopedic pillows in which the comfort layer fill chambers are permanently attached to the adjustable orthopedic pillow, for example, the embodiments of the pillow 100 described with respect to FIGS. 1-6.

In certain embodiments, the inferior section 415 can be positioned within an inferior portion 160C of the comfort layer fill chambers 118A-C. In certain embodiments, the anterior section 420 can extend generally from the inferior portion 160C of each comfort layer fill chamber 118A-C through the anterior portion 160B and into the superior portion 160A. The right section 430A of the piece 410 can be positioned within the superior portion 160A of the comfort layer fill chamber 418A. The left section 430B of the piece 410 can be positioned within the superior portion 160A of the comfort layer fill chamber 118C. The piece 435 can be positioned within the superior portion 160A of the comfort layer fill chamber 118B. The right section 450A of the piece 445 can be positioned within the head support chamber 114A. In some embodiments, the right section 450A can be positioned within a comfort layer fill chamber positioned inferior to the head support fill chamber 114A. The left section 450B of the piece 445 can be positioned within the head support chamber 114C. In some embodiments, the left section 450B can be positioned within a comfort layer fill chamber positioned inferior to the head support fill chamber 114C. In certain embodiments, the piece 435 and/or the piece 440 can be generally trapezoidal in shape. The sections 430A and 430B can be defined by irregular trapezoid shapes. The sections 450A and 450B can be defined by irregular trapezoid shapes.

Figure 10:
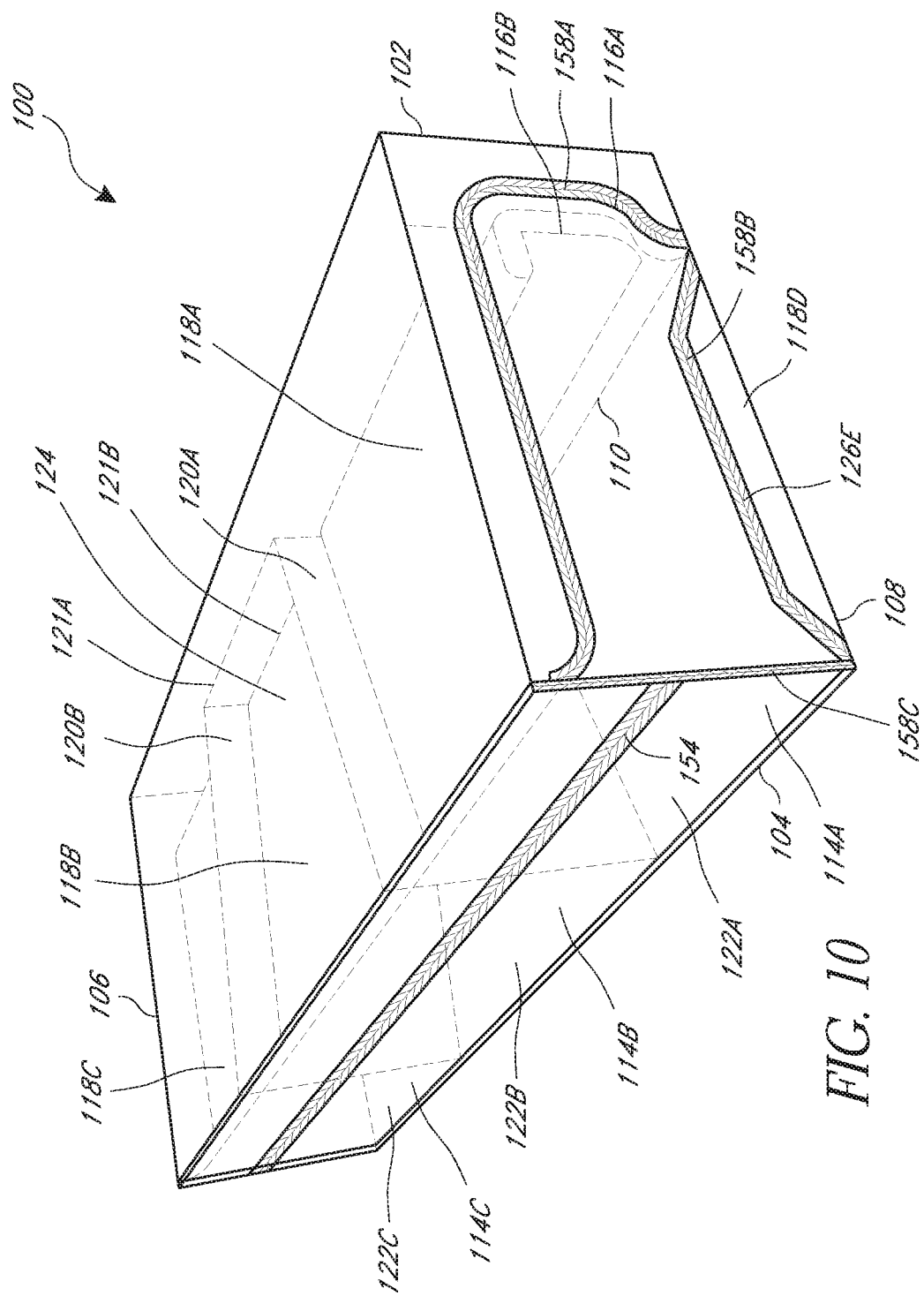
FIG. 10 depicts an embodiment of the pillow 100 in connection with an attachable fill assembly according to an illustrative embodiment of the present invention.

FIG. 10 depicts an embodiment of the pillow 100 in which an encased attachable fill assembly, such as the attachable fill assemblies of FIGS. 8 and 9, is attached to a pillow having head support fill chambers 114A-C and cervical support fill chambers 116A-B by zipper portions 158A, 158B, and 158C. As shown in FIG. 10, the attachable fill assembly forms comfort layer fill chambers 118A-C. In some embodiments, one or more comfort layer fill chambers 118D are also formed beneath the bottom surface of the head support fill chambers 114A-C. The comfort layer fill chambers 118D may be positioned between the head support fill chambers 114A-C and the bottom surface 108 of the pillow 100. Although zippers portions 158A, 158B, and 158C are shown in FIG. 10, other attachment mechanisms, such as ties, hook and loop fasteners, or the like, may be used to attach the attachable fill assembly to pillow 100.

Figure 11:
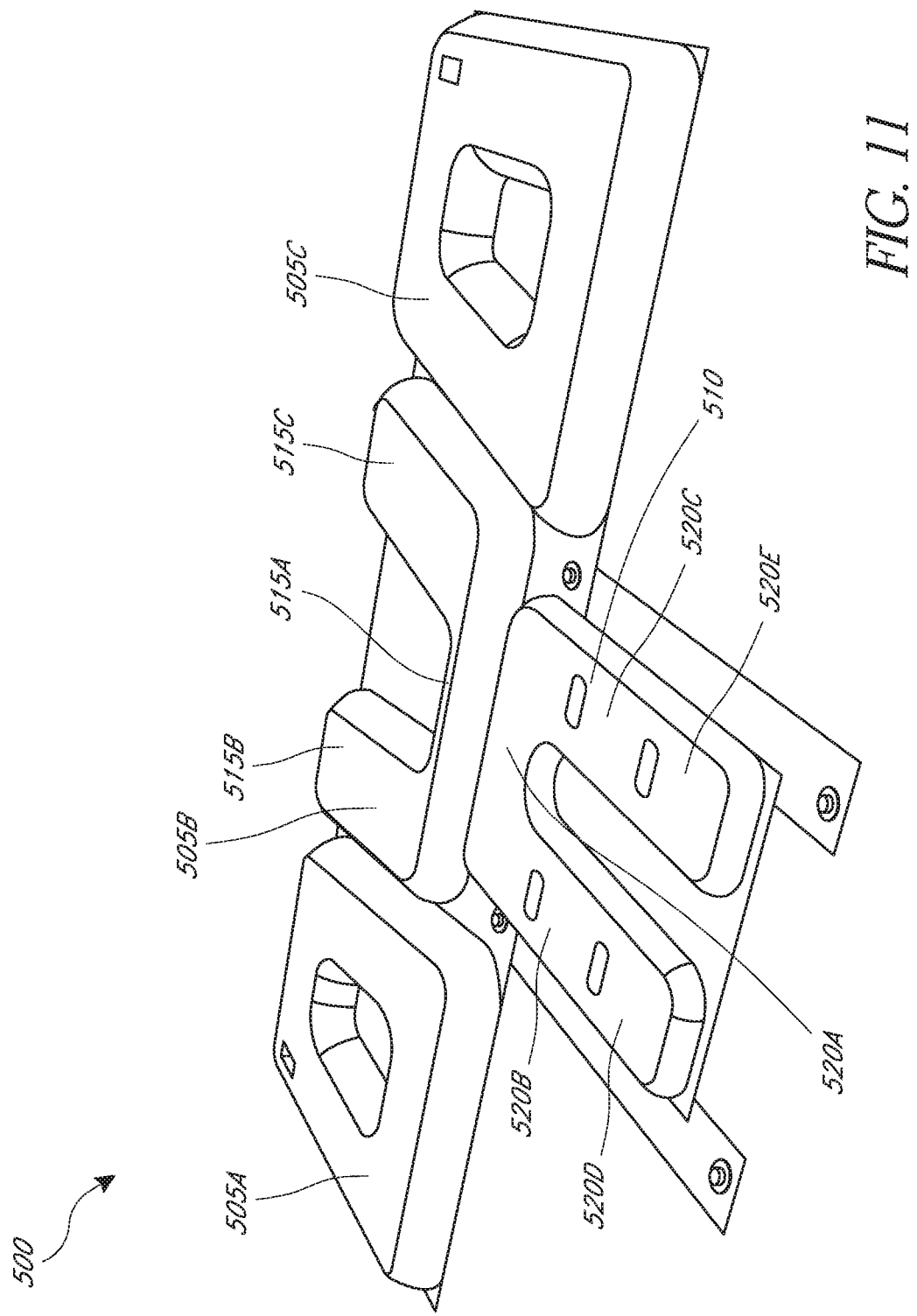
FIG. 11 depicts a perspective view of an inflatable filling assembly 500 in accordance with an illustrative embodiment of the present invention.
Figure 12:
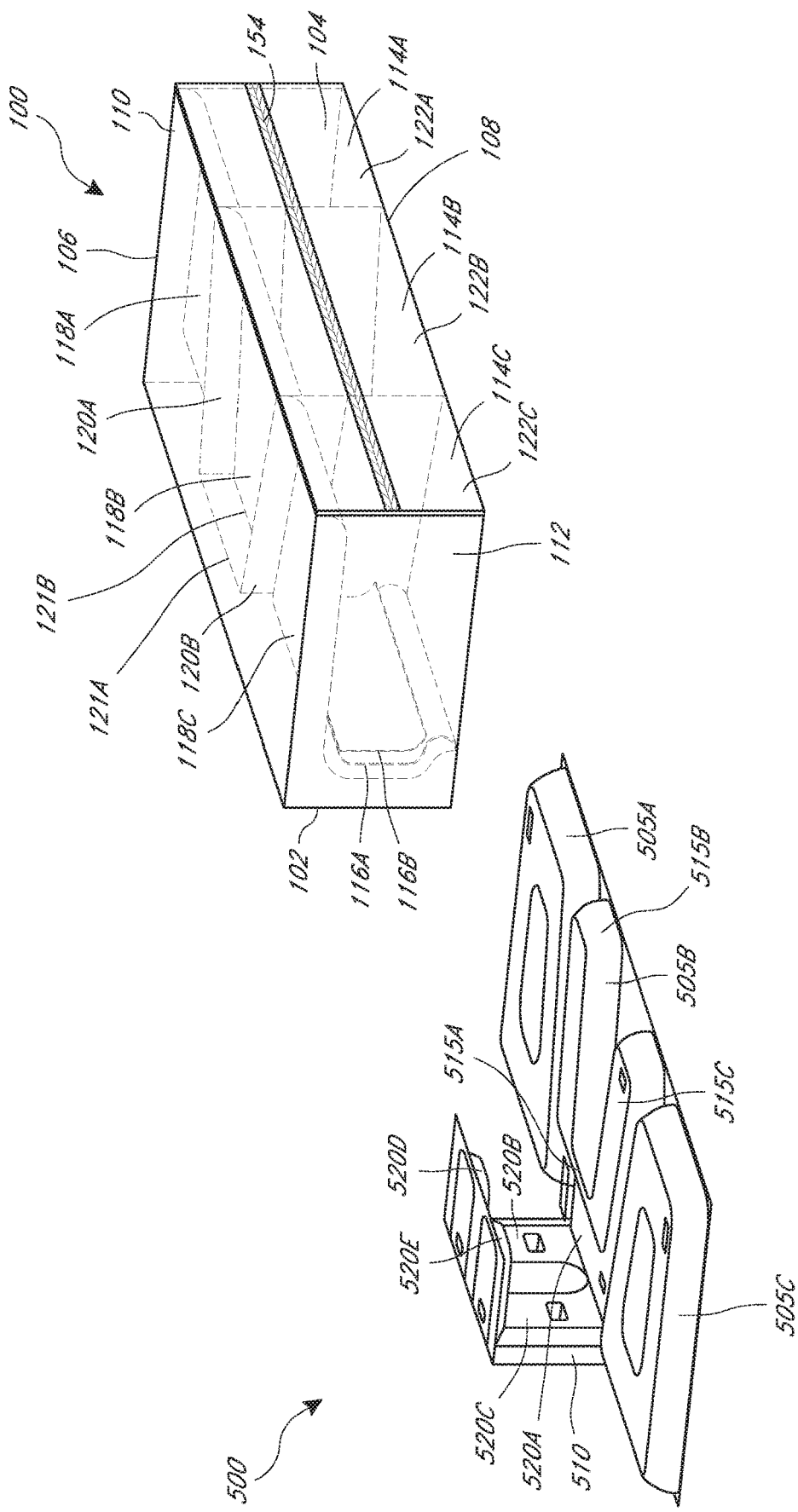
FIG. 12 depicts a perspective view of the inflatable filling assembly 500 and the pillow 100.

FIG. 11 depicts an embodiment of an inflatable filling assembly 500. FIG. 12 depicts an example of a position of the inflatable filling assembly 500 as it can be positioned within the pillow 100. The pillow 100 is shown for reference with internal features shown in dashed lines. In certain embodiments, the inflatable filling assembly 500 includes a plurality of inflatable chambers configured for use in an adjustable orthopedic pillow, such as the adjustable orthopedic pillow 100. The plurality of inflatable chambers can include a plurality of head support inflatable chambers 505A-C and a cervical support inflatable chamber 510. In certain embodiments, the inflatable chambers 505A-C and cervical support inflatable chamber 510 can be connected to one another. Alternatively, one or more of the inflatable chambers 505A-C and the cervical support inflatable chamber 510 can be separate components. The inflatable filling assembly 500 can be positioned within the pillow 100 to act as a filling material in various chambers of the pillow 100.

In certain embodiments, the inflatable chamber 505A can be positioned within the head support fill chamber 114A, the inflatable chamber 505B can be positioned within the head support fill chamber 114B, and the inflatable chamber 505C can be positioned within the head support fill chamber 114C. In certain embodiments, the head support inflatable chamber 505A and/or the head support inflatable chamber 505C can have generally irregular trapezoid shapes. In certain embodiments, the head support inflatable chamber 505A and/or the head support inflatable chamber 505C can have an inflatable perimeter forming an irregular trapezoid shape with an opening in its center. In certain embodiments, the head support inflatable chamber 505B can have be generally U-shaped. The head support inflatable chamber 505B can have a first portion 515A extending generally along a right-left axis, a second portion 515B extending posteriorly and rightward from a right end of the portion 515A, and a third portion 515C extending posteriorly and leftward from a left end of the portion 515A.

In certain embodiments, the cervical support inflatable chamber 510 can be positioned within the primary cervical support fill chamber 116A. In certain embodiments, the cervical support inflatable chamber 510 can be positioned within the secondary cervical support fill chamber 116B. In certain embodiments, the cervical support inflatable chamber 510 can be positioned within the comfort layer fill chamber 118B. In certain embodiments, a portion of the cervical support inflatable chamber 510 can be positioned within the anterior portion 160C of the comfort layer fill chamber 118B and a portion of the inflatable chamber 510 can be positioned within the superior portion 160A of the comfort layer fill chamber 118B. A portion of the inflatable chamber 510 can also extend about the curved portion 126B of the divider 124. In certain embodiments, the cervical support inflatable chamber 510 assume a flexed shape. In some embodiments, the cervical support inflatable chamber 510 can be generally U-shaped. When positioned in the pillow 100, the chamber 510 can have a first portion 520A extending generally along a right-left axis, a second portion 520B extending superiorly from a right end of the portion 520A, and a third portion 520C extending superiorly from a left end of the portion 520A. In certain embodiments, the second portion 520B can extend to a fourth portion 520D that extends posteriorly from a superior end of the second portion 520B and a fifth portion 520E that extends posteriorly from the superior end of the third portion 520C. In certain embodiments, one or more arms may extend between an inferior section of the chamber 510 to a superior section of the chamber 510 to provide support for the superior section of the chamber 510. In some embodiments, one or more arms may extend between an inferior and anterior segment of the chamber 510 to a superior and posterior segment of the chamber 510. In certain embodiments, the inflatable cervical support chamber 510 can be inflated within the pillow 100 to provide an approximate Fibonacci spiral shape beneath the neck of a user. Although a single inflatable chamber 510 is shown in FIG. 11, in certain embodiments, the inflatable filling assembly can include e.g., 1, 2, 3, 4, 5.6 or more inflatable chambers 510. In certain embodiments, the inflatable filling assembly 500 can include a first cervical support inflatable chamber positioned within the first section 122A of the pillow 100, a second cervical support inflatable chamber positioned within the second section 122B of the pillow 100, and a third cervical support inflatable chamber positioned within the third section 122C of the pillow 100.

The inflatable chambers 505A-C and 510 can be inflated using an inflation fluid such as air, water, gel or other thermo-regulatory fluid mediums. In certain embodiments, one or more of the inflatable chambers 505A-C and 510 can be foam filled inflatable air chambers. In certain embodiments, each inflatable chamber 505A-C and 510 can include one or more valves, such as a check valve or a button release valve, to actuate and/or control the inflow and/or outflow of the inflation fluid (e.g., air, water, gel or a gas) into and/or out of the inflatable air chambers 505A-C and 510 e.g., there may be a separate in-port and an out-port for each inflatable chamber, allowing circulation of the fluid into/out of each chamber for temperature control with warmed or cooled fluids. In some embodiments, one or more of the inflatable chambers 505A-C and 510 can be inflated or at least partially inflated prior to introduction into the pillow 100. In certain embodiments, one or more of the inflatable chambers 505A-C and 510 can be inflated or at least partially inflated within the pillow 100. In certain embodiments, one or more of the inflatable chambers 505A-C and 510 can be inflated manually, for example, using one or more manual pumps. In certain embodiments, the inflatable assembly 500 can include one or more electric pumps or other electronic filling devices in connection with one or more of the inflatable chambers 505A-C and 510 for inflation of the inflatable chambers. In certain embodiments, inflation of one or more of the inflatable chambers 505A-C and 510 can be activated using an electronic device, such as a remote control. In certain embodiments, an electronic device can allow for a selection of one or more of the inflatable chambers 505A-C and 510 for inflation. In some embodiments, an electronic device can be used for selecting an inflation amount of one or more of the inflatable chambers 505A-C and 510. In certain embodiments, the inflatable filling assembly 500 can include one or more receivers configured to receive a signal from an electronic device. In certain embodiments, the one or more receivers can receive inflation instructions from an external device. In certain embodiments, the inflatable assembly 500 can include one or more processors configured to process instructions received at the receiver. The one or more processors can also control inflation one or more of the inflatable chambers 505A-C and 510. For example, the one or more processors can provide instructions to the one or more electric pumps or other electronic filling devices to inflate one or more of the inflatable chambers 505A-C and 510. In certain embodiments, one or more fluids can be circulated within the inflatable chambers 505A-C and 510 to provide temperature therapy, for example, by changing the temperature within the inflatable chambers 505A-C. In certain embodiments, an electronic device can cause the circulation of one or more heated or cooled fluids, such as air, water, gel or other thermo-regulatory fluid mediums to provide temperature control.

Figure 14:
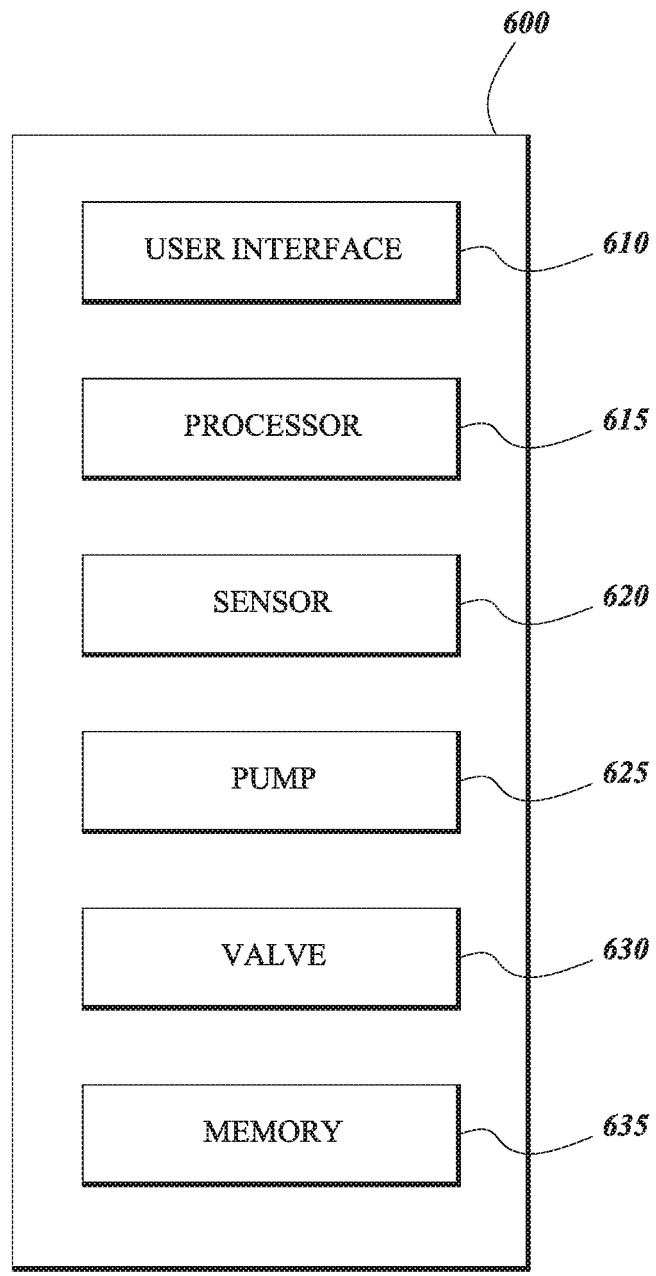
FIG. 14 depicts a block diagram of an inflation system 600 according to an illustrative embodiment of the present invention.

FIG. 14 depicts a block diagram of system 600 that can be used with an inflatable or fillable pillow or filling assembly, such as inflatable filling assembly 500. The system 600 can include one or more pumps or other filling devices 625 configured to inflate or fill an inflatable pillow or inflatable filling assembly with an inflation fluid (e.g., air, water, gel or a gas). For example, in certain embodiments, the pumps 625 can be configured to inflate or fill one or more of the inflatable chambers 505A-C and 510. In certain embodiments, the pumps 625 can include manual and/or electronic pumps. In certain embodiments, the one or more pumps 625 can be part of an inflatable pillow or inflatable filling assembly 500. In certain embodiments, the one or more pumps can be attachable/detachable from an inflatable pillow or inflatable filling assembly 500.

In certain embodiments, the inflation system 600 can include one or more valves 630. The valves 630 can be coupled to an inflatable pillow or inflatable filling assembly, such as inflatable filling assembly 500 to allow the inflation fluid to flow into and/or out of the inflatable pillow or inflatable filling assembly. For example, in certain embodiments, each of the inflatable chambers 505A-C and 510 can include a valve 630 to allow for inflation fluid inflow and/or outflow. In some embodiments, each valve 630 can be coupled to a pump 625. In certain embodiments, a plurality of valves 630 can be coupled to a single pump 625. In certain embodiments, the valves 630 can include check valves, button release valves, or any other suitable valve type.

In certain embodiments, the inflation system 600 can include one or more processors 615. The processors 615 can be configured to control inflation of an inflatable pillow or inflatable filling assembly, such as inflatable filling assembly 500. For example, in some embodiments, the one or more processors can control inflation of one or more of the inflatable chambers 505A-C and 510. In certain embodiments, the processors 615 can be configured to communicate with one or more of the pumps 625 and/or the valves 630. In certain embodiments, the one or more processors 615 can provide instructions to the one or more pumps 625 to inflate and/or deflate one or more of the inflatable chambers 505A-C and 510. In certain embodiments, the one or more processors 615 can provide instructions to open and/or close one or more of the valves 630. In certain embodiments, the one or more processors 615 can provide instructions to the one or more pumps 625 to inflate/deflate (or fill or un-fill) at one or more of a defined rate, a defined rhythm, a defined amplitude of pressure, and a defined amplitude of volume. In certain embodiments, the one or more processors 615 can control the one or more pumps 625 to inflate/deflate (or fill or un-fill) the chambers 505A-C and 510 using one or more inflation or filling patterns, for example, to cause a pattern of head and/or spinal movements such as flexion, extension, lateral flexion, rotation, or combinations of any of the foregoing movements for therapeutic purposes. For example, in certain embodiments, the one or more processors 615 can control the one or more pumps 625 to cause alternating inflation and deflation (or filling or un-filling) of one of the chambers 505A-C and 510 in correlation with a defined therapeutic pattern. In certain embodiments, the one or more processors 615 can control the one or more pumps 625 to inflate and/or deflate (or fill or un-fill) different chambers 505A-C and 510 at different times in correlation with a defined therapeutic pattern. In certain embodiments, the one or more processors 615 can control the one or more pumps 625 to inflate and/or deflate (or fill or un-fill) one or more of the chambers 505A-C and 510 to cause movement of the head of the user from one of the chambers 505A-C and 510 to another of chambers 505A-C and 510. In certain embodiments, the processors 615 can control the one or more pumps 625 to cause a pattern of head movements between one or more of the chambers 505A-C and 510. In certain embodiments, the processors 615 can control the one or more pumps 625 to cause inflation or filling in an inflatable or fillable pillow or inflatable or fillable filling assembly using a wave pattern, for example, by causing inflation or filling at a front section of the inflatable or fillable pillow or inflatable or fillable filling assembly followed by inflation or filling at a rear section of the inflatable or fillable pillow or inflatable or fillable filling assembly, or vice versa. Similarly, the processors 615 can control the one or more pumps 625 to cause deflation or un-filling in an inflatable or fillable pillow or inflatable or fillable filling assembly using a wave pattern, for example, by causing deflation or un-filling at a front section of the inflatable or fillable pillow or inflatable or fillable filling assembly followed by deflation or un-filling at a rear section of the inflatable or fillable pillow or inflatable or fillable filling assembly, or vice versa. Use of a wave pattern can facilitate inflation and/or deflation (or fill or un-fill) first beneath the neck of a user and second beneath the head of the user, or vice versa. For example, in certain embodiments, the processor 615 can control the one or more pumps 625 to cause inflation and/or deflation (or filling or un-filling) first in the chamber 510 and second in the chamber 505B, or vice versa. The wave pattern can be used for certain therapeutic treatments. Although inflation/deflation (or filling or un-filling) in only a front section or rear section are discussed, in certain embodiments, inflation/deflation (or filling or un-filling) can occur sequentially in more than two chambers from a front-most chamber to a rear-most chamber, or vice-versa.

In certain embodiments, the one or more processors 615 can be integrated into an inflatable or fillable pillow or inflatable fillable filling assembly, such as inflatable filling assembly 500. In other embodiments, the one or more processors 615 can be part of an external device, such as a remote control, which can communicate through a wireless or wired connection with the inflatable or fillable pillow or inflatable or fillable filling assembly.

In certain embodiments, the inflation system 600 can include one or more sensors 620. The sensors 620 can measure and/or monitor one or more inflation or filling parameters such as, for example, the pressure and/or volume within an inflatable or fillable pillow or inflatable or fillable filling assembly, such as inflatable filling assembly 500. In certain embodiments, the sensors 620 can measure one or more inflation or filling parameters of one or more of the chambers 505A-C and 510. In certain embodiments, the one or more sensors 620 can include one or more pressure sensors, such as pressure transducers, for measuring pressure within one or more of the chambers 505A-C and 510. In certain embodiments, the sensors 620 can include one or more volume sensors for measuring the volume of inflation fluid within one or more of the chambers 505A-C and 510. In certain embodiments, the sensors 620 can include one or more volume flow meters to measure the velocity of inflow and/or outflow of inflation fluid into and/or out one or more of the chambers 505A-C and 510.

In certain embodiments, the one or more sensors 620 can be in communication with the one or more processor 615*s*. In certain embodiments, the processors 615 can be configured to receive and/or process data from the one or more sensors 620. In certain embodiments, the processors 615 can be configured to control inflation and/or deflation (or filling or un-filling) based on data from the one or more sensors 620. For example, in certain embodiments, the processors 615 can be configured to cause inflation and/or deflation (or filling or un-filling) within the one or more chambers 505A-C and 510 based on minimum and/or maximum inflation parameter. The processors 615 can be configured to cause inflation and/or deflation (or filling or un-filling) of one or more of the chambers 505A-C and 510 if one or more of the sensors 620 detects that a parameter, such as pressure or volume, of one or more of the inflation chambers 505A-C and 510 are outside of a defined minimum and/or maximum or outside of a defined parameter range. In certain embodiments, defined minimums, maximums, and/or ranges can be selected within safety tolerances or to prevent or inhibit user pain or discomfort.

In certain embodiments, one or more measurements from the sensors 620 can be recorded or stored in a memory 635. In certain embodiments, one or more measurements from the sensors 620 can be compared with previous measurements for determining therapeutic effectiveness, improvement, or decline. For example, in certain embodiments, measurements can be compared to determine changes, for example, improvement or decline, in ranges over which a user experiences pain or discomfort or does not experience pain or discomfort. In certain embodiments, data measured by the sensors 620 can be used for area/volume graphing or documentation, which can be used to achieve therapeutic benefit for the user e.g., facilitating or guiding of programming of the electronic controller of each chamber's inflation/deflation, which can maximize or increase therapeutic mobility and user improvement and the documentation of improvement (e.g., over time with consecutive therapeutic sessions) can generate and, optionally output a display showing pain-free ranges of inflation/deflation of the inflatable chambers.

In certain embodiments, the one or more sensors 620 can include sensors for detecting patient parameters. For example, in certain embodiments, the one or more sensors 620 can include one or more sensors, such as audio sensors configured to detect snoring, apnea, or breathing patterns of the patient. In certain embodiments, the one or more sensors 620 can include one or more sensors, such as position or motion sensors, configured to detect the position and/or movement of the head and/or neck of the patient. In certain embodiments, the processor 615 can be configured to control inflation and/or deflation based on the sensors for detecting patient parameters. For example, in certain embodiments, if snoring, apnea, or abnormal breathing is detected, the processor can control inflation and/or deflation (or filling or un-filling) of one or more of the chambers 505A-C and 510 to cause movement of the head or neck of the user, for example, to cause the user to roll from their back to their side.

In certain embodiments, the one or more sensors 620 can be integrated into an inflatable or fillable pillow or inflatable or fillable filling assembly, such as inflatable filling assembly 500. In other embodiments, the sensors 620 can be part of an external device which can communicate through a wireless or wired connection with the inflatable or fillable pillow or inflatable or fillable filling assembly.

In certain embodiments, the memory 635 can be integrated into an inflatable or fillable pillow or inflatable or fillable filling assembly, such as inflatable filling assembly 500. In other embodiments, the memory 635 can be part of an external device which can communicate through a wireless or wired connection with the inflatable or fillable pillow or inflatable or fillable filling assembly.

In certain embodiments, the inflation system 600 can include a user interface 610. The user interface 610 can allow a user or treating clinician to control the inflation system 600. For example, in certain embodiments, the user interface 610 can be operated to initiate and/or stop inflation and/or deflation (or filling or un-filling). In certain embodiments, the user interface 610 can be operated to initiate or store one or more therapeutic inflation/deflation (or filling or un-filling) patterns or treatments as described herein. In certain embodiments, the user interface 610 can be operated to input patient or treatment data to be stored by the memory 635. In certain embodiments, the user interface 610 can be used to retrieve and/or view data stored in the memory 635.

In certain embodiments, the user interface 610 can be integrated into an inflatable or fillable pillow or inflatable or fillable filling assembly, such as inflatable filling assembly 500. In other embodiments, the user interface 610 can be part of an external device, such as a remote control, which can communicate through a wireless or wired connection with the inflatable or fillable pillow or inflatable or fillable filling assembly.

In certain embodiments, an attachable pad may be connected to an exterior of the pillow 100 having a fluid such as air, water, gel or other thermo-regulatory fluid mediums, to provide temperature control. Such a pad can be heated or cooled prior to connection to the pillow 100. Such a pad may be similar in shape and structure to the attachable comfort layer fill chambers shown in FIGS. 7-9. In some embodiments, the attachable pad may be generally H-shaped or generally U-shaped. The pad can include one or more cushioned or inflatable portions configured to provide additional support to a user. For example, the pad can include one or more cushioned or inflatable portions configured to provide support to the head of the user. In certain embodiments, the pad can include one or more cushioned or inflatable portions configured to provide support to a neck of the user.

Figure 13A:
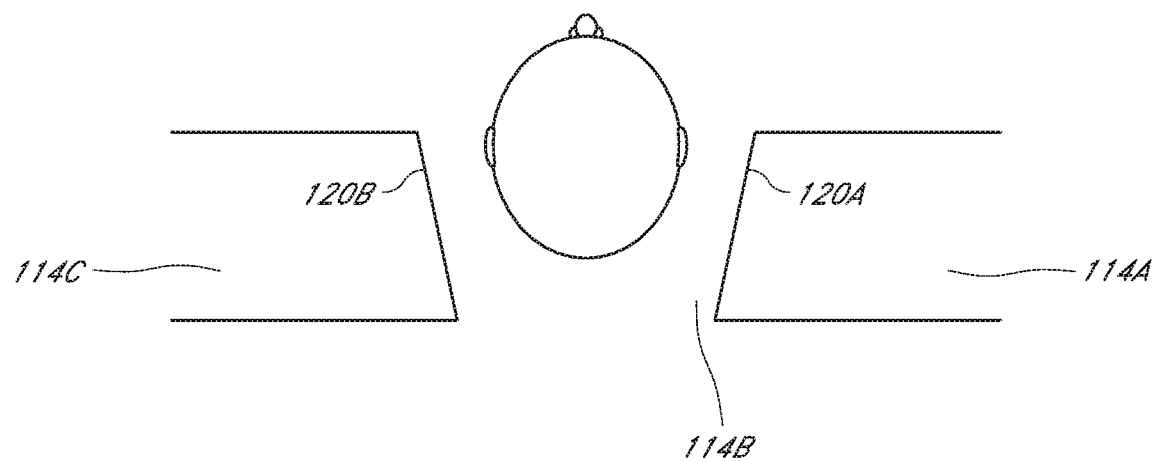
FIG. 13A depicts a posterior schematic view of an illustrative example of a user lying on a section of the pillow 100.
Figure 13B:
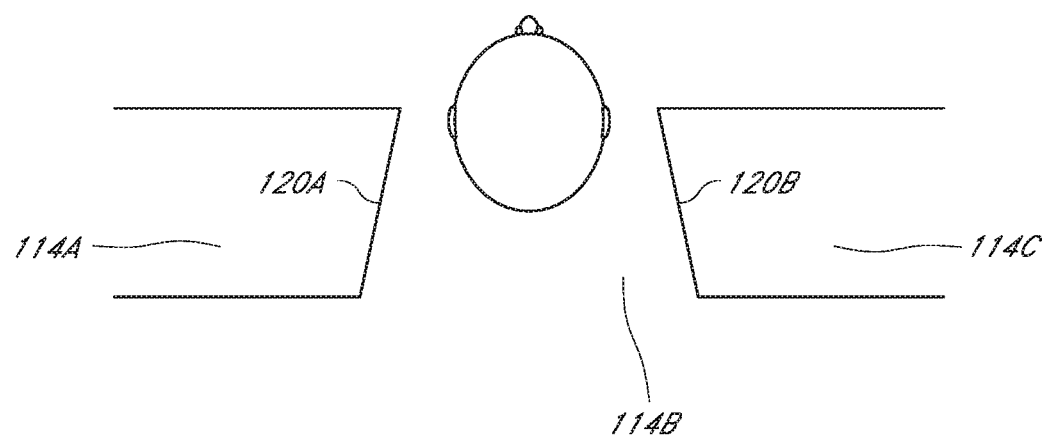
FIG. 13B depicts a posterior schematic view illustrative example of a user lying on a section of the pillow 100.

FIGS. 13A and 13B each depict a posterior schematic view showing the positions of the dividers 120A and 120B between the head chambers 114A-C with a user lying over the head support fill chamber 114B. The inferior edge and superior edge of each of the dividers 120A and 120B can be chamfered to allow the adjustable orthopedic pillow to provide support to a relatively larger individual and a relatively smaller individual. The chamfering of the edges of the dividers 120A and 120B can shape the head support fill chamber 114B by orienting the dividers 120A and 120B to accommodate both relatively larger and relatively smaller heads between the head support fill chambers 114A and 114C.

In some embodiments, the dividers 120A and 120B may extend laterally and superiorly from the bottom surface 108 towards the top surface 106. In such embodiments, a lateral dimension of the head support fill chamber 114B may be greater at a superior end of the head support fill chamber 114B than at an inferior end of the head support fill chamber 114B. In such embodiments, the head support fill chamber 114B can be shaped and/or dimensioned to accommodate a relatively larger head when the relatively larger head is positioned on the top surface 106 of the pillow 100 over the head support fill chamber 114B, for example, as shown in FIG. 13A. The head support fill chamber 114B can also be shaped and/or dimensioned to accommodate a relatively smaller head when the pillow is positioned so that the bottom surface 108 is superior to the top surface 106 and the relatively smaller head is positioned on the bottom surface 108 over the head support fill chamber 114B, for example, as shown in FIG. 13B. As shown in FIG. 13B, the pillow 100 has been rotated 180° about a horizontal (left-right axis).

In some embodiments, the dividers 120A and 120B may extend medially and superiorly from the bottom surface 108 towards the top surface 106. In such embodiments, a lateral dimension of the head support fill chamber 114B may be greater at an inferior end of the head support fill chamber 114B than at an inferior end of the head support fill chamber 114B. In such embodiments, the head support fill chamber 114B can be shaped and/or dimensioned to accommodate a relatively smaller head when the relatively smaller head is positioned on the top surface 106 over the head support fill chamber 114B. In such embodiments, the head support fill chamber 114B can be shaped and/or dimensioned to accommodate a relatively larger head when the relatively larger head is positioned on the bottom surface 108 over the head support fill chamber 114B.

While the above detailed description has shown, described, and pointed out novel features of the development as applied to various embodiments, it will be understood that various omissions, substitutions, and changes in the form and details of the devices illustrated may be made by those skilled in the art without departing from the spirit of the development. As will be recognized, the present development may be embodied within a form that does not provide all of the features and benefits set forth herein, as some features may be used or practiced separately from others. All changes which come within the meaning and range of equivalency of the claims are to be embraced within their scope.

The foregoing description details certain embodiments of the systems, devices, and methods disclosed herein. It will be appreciated, however, that no matter how detailed the foregoing appears in text, the systems, devices, and methods may be practiced in many ways. As is also stated above, it should be noted that the use of particular terminology when describing certain features or aspects of the invention should not be taken to imply that the terminology is being redefined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment may be included with other depicted embodiments in any combination. For example, any of the various components described herein and/or depicted in the Figures may be combined, interchanged or excluded from other embodiments.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone. C alone, A and B together, A and C together, B and C together, and/or A, B, and C together, etc.). In those instances where a convention analogous to "at least one of A. B, or C, etc." is used, in general such a construction is intended in the sense one having skill in the art would understand the convention (e.g., "a system having at least one of A, B. or C" would include but not be limited to systems that have A alone, B alone. C alone, A and B together, A and C together. B and C together, and/or A. B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The term "comprising" as used herein is synonymous with "including," "containing," or "characterized by," and is inclusive or open-ended and does not exclude additional, unrecited elements or method steps.

The above description discloses several methods of manufacture and materials of the present development. This development is susceptible to modifications in the methods and materials, as well as alterations in the fabrication methods and equipment. Such modifications will become apparent to those skilled in the art from a consideration of this disclosure or practice of the development disclosed herein. Consequently, it is not intended that this development be limited to the specific embodiments disclosed herein, but that it cover all modifications and alternatives coming within the true scope and spirit of the development as embodied in the attached claims.

While the above detailed description has shown, described, and pointed out novel features of the improvements as applied to various embodiments, it will be understood that various omissions, substitutions, and changes in the form and details of the device or process illustrated may be made by those skilled in the art without departing from the spirit of the invention. As will be recognized, the present invention may be embodied within a form that does not provide all of the features and benefits set forth herein, as some features may be used or practiced separately from others. The scope of the invention is indicated by the appended claims rather than by the foregoing description. All changes which come within the meaning and range of equivalency of the claims are to be embraced within their scope.

What is claimed is:

1. An adjustable orthopedic pillow, comprising:
    a rear surface;
    a front surface;
    a left side surface;
    a right side surface;
    a top surface;
    a bottom surface;
    a plurality of sections comprising a left section, a right section, and a center section, wherein the left section is at least partially separated from the center section by a first divider extending from the rear surface of the pillow towards the front surface of the pillow and extending from the bottom surface of the pillow towards the top surface of the pillow, wherein the right section is at least partially separated from the center section by a second divider extending from the rear surface of the pillow towards the front surface of the pillow and extending from the bottom surface of the pillow towards the top surface of the pillow, wherein each of the left section, the right section, and the center section comprises:
        a head support fill chamber extending anteriorly from the rear surface of the pillow at least partially towards the front surface of the pillow and extending superiorly from the bottom surface of the pillow at least partially towards the top surface of the pillow, the head support fill chamber being configured to receive one or more filling materials;
        a comfort layer fill chamber positioned between the head support fill chamber and the top surface of the pillow and between the head support fill chamber and the front surface of the pillow, the comfort layer fill chamber being configured to receive one or more filling materials;
        a primary cervical support fill chamber positioned between at least a portion of the head support fill chamber and at least a portion of the comfort layer fill chamber, the primary cervical support fill chamber comprising an opening at a superior portion of the primary cervical support fill chamber, the primary cervical support fill chamber being configured to receive one or more filling materials; and
        a secondary cervical support fill chamber positioned between at least a portion of the head support fill chamber and at least a portion of primary cervical support fill chamber, the secondary cervical support fill chamber comprising an opening at an inferior portion of the secondary cervical support fill chamber, the secondary cervical support fill chamber being configured to receive one or more filling materials; and
    a third divider extending from the left side surface of the pillow to the right side surface of the pillow and from the rear surface of the pillow towards the front surface of the pillow, wherein the third divider separates each of the head support fill chambers from each of the comfort layer fill chambers;
    wherein the head support fill chamber of the left section is separated from the head support fill chamber of the center section by the first divider and the head support fill chamber of the right section is separated from the head support fill chamber of the center section by the second divider.

2. The adjustable orthopedic pillow of claim 1, further comprising a zipper extending along the rear surface of the pillow, the zipper defining an opening allowing access to at least one of the plurality of sections.

3. The adjustable orthopedic pillow of claim 2, wherein the head support fill chamber, the comfort layer fill chamber, the primary cervical support fill chamber, and the secondary cervical support fill chamber of the at least one of the plurality of sections is accessible via the opening defined by the zipper.

4. The adjustable orthopedic pillow of claim 1,
    wherein the first divider and the second divider are angled medially toward the front surface of the pillow such that the head support fill chamber of the center section resembles a generally trapezoidal shape, smaller in measure in an anterior dimension than in a posterior dimension, and each of the head support fill chambers of the left section and the right section are shaped as irregular complementary trapezoids.

5. The adjustable orthopedic pillow of claim 4, wherein the primary cervical support fill chamber of the left section, the primary cervical support fill chamber of the center section, and the primary cervical support fill chamber of the right section are each part of a single continuous primary cervical support fill chamber extending from the left section to the right section.

6. The adjustable orthopedic pillow of claim 1, further comprising a strap secured to a posterior portion of the secondary cervical support fill chamber of one of the plurality of sections.

7. The adjustable orthopedic pillow of claim 1, further comprising a foam support extending from the head support fill chamber of one of the plurality of sections into the comfort layer fill chamber of the same section of the plurality of sections.

8. The adjustable orthopedic pillow of claim 1, further comprising a plurality of inflatable fluid chambers, at least one inflatable fluid chamber positioned within the head support fill chamber of at least one of the plurality of sections and at least one inflatable fluid chamber positioned within the primary cervical support fill chamber or the secondary cervical support fill chamber of at least one of the plurality of sections.

9. The adjustable orthopedic pillow of claim 8, further comprising a receiver and a processor, the processor configured to control inflation of the plurality of inflatable fluid chambers in response to receiving a signal at the receiver.

10. The adjustable orthopedic pillow of claim 1, wherein the first divider and the second divider each comprise a chamfered portion.

11. The adjustable orthopedic pillow of claim 1, wherein at least a portion of the primary cervical support fill chamber is positioned inferior to a portion of the secondary cervical support fill chamber.

12. An adjustable orthopedic pillow, comprising:
a rear surface;
a front surface;
a left side surface;
a right side surface;
a top surface;
a bottom surface;
a plurality of sections comprising a left section, a right section, and a center section, wherein the left section is at least partially separated from the center section by a first divider extending from the rear surface of the pillow towards the front surface of the pillow and extending from the bottom surface of the pillow towards the top surface of the pillow, wherein the right section is at least partially separated from the center section by a second divider extending from the rear surface of the pillow towards the front surface of the pillow and extending from the bottom surface of the pillow towards the top surface of the pillow, wherein each of the left section, the right section, and the center section comprises:
a head support fill chamber extending anteriorly from the rear surface of the pillow at least partially towards the front surface of the pillow and extending superiorly from the bottom surface of the pillow at least partially towards the top surface of the pillow, the head support fill chamber being configured to receive one or more filling materials;
a comfort layer fill chamber positioned between the head support fill chamber and the top surface of the pillow and between the head support fill chamber and the front surface of the pillow, the comfort layer fill chamber being configured to receive one or more filling materials; and a plurality of cervical support fill chambers positioned between the head support fill chamber and an anterior section of the comfort layer fill chamber, wherein at least one of the plurality of cervical support fill chambers comprises an opening at a superior portion of the cervical support fill chamber and at least one of the cervical support fill chambers comprises an opening at an inferior portion of the cervical support fill chamber, the plurality of cervical support fill chambers being configured to receive one or more filling materials; and
a third divider extending from the left side surface of the pillow to the right side surface of the pillow and from the rear surface of the pillow towards the front surface of the pillow, wherein the third divider separates each of the head support fill chambers from each of the comfort layer fill chambers;
wherein the head support fill chamber of the left section is separated from the head support fill chamber of the center section by the first divider and the head support fill chamber of the right section is separated from the head support fill chamber of the center section by the second divider.

13. The adjustable orthopedic pillow of claim 12, wherein the plurality of cervical support fill chambers comprise:
a primary cervical support fill chamber positioned between at least a portion of the head support fill chamber and at least a portion of the comfort layer fill chamber, the primary cervical support fill chamber comprising an opening at a superior portion of the primary cervical support fill chamber;
a secondary cervical support fill chamber positioned between at least a portion of the head support fill chamber and at least a portion of primary cervical support fill chamber, the secondary cervical support fill chamber comprising an opening at an inferior portion of the secondary cervical support fill chamber.

14. The adjustable orthopedic pillow of claim 12, wherein the plurality of cervical support fill chambers comprise a series of alternating first cervical support fill chambers and second cervical support fill chambers, each first cervical support fill chamber comprising an opening at a superior portion of the first cervical support fill chamber and each second cervical support fill chamber comprising an opening at an inferior portion of the second cervical support fill chamber.

15. The adjustable orthopedic pillow of claim 12, wherein a portion of the third divider separates the anterior section of the comfort layer fill chamber and an anterior-most cervical support fill chamber of the plurality of cervical support fill chambers, wherein the plurality of cervical support fill chambers are positioned in a nesting configuration extending from the divider towards a posterior portion of the pillow.

16. The adjustable orthopedic pillow of claim 12, further comprising a strap secured to a posterior-most cervical support fill chamber of one of the plurality of sections, the strap configured to secure a foam support to a posterior wall of the posterior-most cervical support fill chamber of the one of the plurality of sections.

17. An adjustable orthopedic pillow, comprising:
a rear surface;
a front surface;
a left side surface;
a right side surface;
a top surface;
a bottom surface;

a plurality of sections comprising a left section, a right section, and a center section, wherein the left section is at least partially separated from the center section by a first divider extending from the rear surface of the pillow towards the front surface of the pillow and extending from the bottom surface of the pillow towards the top surface of the pillow, wherein the right section is at least partially separated from the center section by a second divider extending from the rear surface of the pillow towards the front surface of the pillow and extending from the bottom surface of the pillow towards the top surface of the pillow, wherein each of the left section, the right section, and the center section comprises:
- a head support fill chamber extending anteriorly from the rear surface of the pillow at least partially towards the front surface of the pillow and extending superiorly from the bottom surface of the pillow at least partially towards the top surface of the pillow, the head support fill chamber being configured to receive one or more filling materials;
- a comfort layer fill chamber positioned between the head support fill chamber and the top surface of the pillow and between the head support fill chamber and the front surface of the pillow, the comfort layer fill chamber being configured to receive one or more filling materials; and
- a cervical support fill chamber positioned between the head support fill chamber and an anterior section of the comfort layer fill chamber, wherein the cervical support fill chamber comprises:
  - a first end comprising an opening;
  - a second end; and
  - a channel extending between the first end and the second end, the channel comprising a first channel portion extending parallel to the front surface of the pillow and a second channel portion extending posteriorly from the first portion, the cervical support fill chamber being configured to receive one or more filling materials; and
- a third divider extending from the left side surface of the pillow to the right side surface of the pillow and from the rear surface of the pillow towards the front surface of the pillow, wherein the third divider separates each of the head support fill chambers from each of the comfort layer fill chambers;
wherein the head support fill chamber of the left section is separated from the head support fill chamber of the center section by the first divider and the head support fill chamber of the right section is separated from the head support fill chamber of the center section by the second divider.

18. The adjustable orthopedic pillow of claim 17, wherein the first end of the cervical support fill chamber is a superior end and the second end of the cervical support fill chamber is an inferior end.

19. The adjustable orthopedic pillow of claim 17, wherein the first end of the cervical support fill chamber is an inferior end and the second end of the cervical support fill chamber is a superior end.

20. The adjustable orthopedic pillow of claim 17, wherein a portion of a posterior wall of the cervical support fill chamber is movable to alter the size of the opening in the first end of the cervical support fill chamber.

\* \* \* \* \*